United States Patent
Johanson et al.

(10) Patent No.: US 7,087,405 B2
(45) Date of Patent: Aug. 8, 2006

(54) NUCLEIC ACIDS ENCODING ANTI-HUMAN αvβ3 AND αvβ5 ANTIBODIES

(75) Inventors: Kyung O Johanson, Bryn Mawr, PA (US); Zdenka Ludmila Jonak, Devon, PA (US); Alexander Taylor, Newton Square, PA (US); Stephen H Trulli, Havertown, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 218 days.

(21) Appl. No.: 10/141,908

(22) Filed: May 9, 2002

(65) Prior Publication Data

US 2003/0004317 A1 Jan. 2, 2003

Related U.S. Application Data

(60) Continuation of application No. 09/694,951, filed on Oct. 24, 2000, now abandoned, which is a division of application No. 09/199,149, filed on Nov. 24, 1998, now Pat. No. 6,160,099.

(51) Int. Cl.
*C12P 21/06* (2006.01)

(52) U.S. Cl. ............... 435/69.1; 536/23.5; 536/23.53; 435/69.6; 435/320.1; 435/325; 530/387.3; 530/388.22

(58) Field of Classification Search ............... 536/23.1, 536/23.53, 24.1, 24.31, 24.33, 23.5; 435/325, 435/326, 326.1, 69.6, 69.1
See application file for complete search history.

(56) References Cited

FOREIGN PATENT DOCUMENTS

| EP | 0 719 859 | 7/1996 |
| WO | WO 97/06791 | 2/1997 |
| WO | WO 99/55369 | 11/1999 |

OTHER PUBLICATIONS

Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987.*
Lin et al Biochemistry USA vol. 14:1559-1563 (1975.*
Rudikoff et al (Proc Natl Acad Sci USA 1982 vol. 79 p. 1979.*
1993/94 Promega Catalog.*
Cabilly et al (Proc. Natl. Acad. Sci. USA 81:3273-3277, 1984.*

* cited by examiner

*Primary Examiner*—Stephen L. Rawlings
(74) *Attorney, Agent, or Firm*—Andrea V. Lockenour; Edward R. Gimmi; Charles M. Kinzig

(57) ABSTRACT

This invention relates to novel humanized and other recombinant or engineered antibodies or monoclonal antibodies to a human $\alpha_v$ subunit-containing heterodimeric integrin receptors and to the genes encoding same. Such antibodies are useful for the therapeutic and/or prophylactic treatment of disorders mediated by such receptors, such as cancer, in human patients.

20 Claims, 13 Drawing Sheets

FIGURE 1A
B9 MURINE HEAVY CHAIN V REGION [SEQ ID NOS 1, 2 AND 38]

```
 Q   V   Q   L   Q   Q   S   G   A   E   L   M   K   P   G
CAA GTT CAG CTT CAA CAG TCT GGA GCT GAG CTG ATG AAG CCT GGG
GTT CAA GTC GAA GTT GTC AGA CCT CGA CTC GAC TAC TTC GGA CCC

A   S   V   K   I   S   C   K   A   T   G   Y   T   F   S
GCC TCA GTG AAG ATA TCC TGC AAG gCT ACT GGC TAC ACA TTC AGT
CGG AGT CAC TTC TAT AGG ACG TTC cGA TGA CCG ATG TGT AAG TCA

S   Y   W   I   E   W   V   K   Q   R   P   G   H   G   L
AGC TAC TGG ATA GAG TGG GTA AAG CAG AGG CCT GGA CAT GGC CTT
TCG ATG ACC TAT CTC ACC CAT TTC GTC TCC GGA CCT GTA CCG GAA

E   W   I   G   E   I   L   P   R   S   G   N   T   N   Y
GAG TGG ATT GGA GAG ATT TTA CCT AGA AGT GGT AAT ACT AAC TAC
CTC ACC TAA CCT CTC TAA AAT GGA TCT TCA CCA TTA TGA TTG ATG

N   E   K   F   K   G   K   A   T   F   T   A   E   T   S
AAT GAG AAG TTC AAG GGC AAG GCC ACA TTC ACT GCA GAA ACA TCC
TTA CTC TTC AAG TTC CCG TTC CGG TGT AAG TGA CGT CTT TGT AGG

S   N   T   A   Y   M   Q   L   S   S   L   T   P   E   D
TCC AAC ACA GCC TAC ATG CAA CTC AGC AGC CTG ACA CCT GAG GAC
AGG TTG TGT CGG ATG TAC GTT GAG TCG TCG GAC TGT GGA CTC CTG

S   A   V   Y   Y   C   S   S   R   G   V   R   G   S   M
TCT GCC GTC TAT TAC TGT TCA AGT CGC GGC GTC AGG GGC TCT ATG
AGA CGG CAG ATA ATG ACA AGT TCA GCG CCG CAG TCC CCG AGA TAC

D   Y   W   G   Q   G   T   S   V   T   V   S   S
GAC TAC TGG GGT CAA GGA ACC TCA GTC ACC GTC TCC TCA
CTG ATG ACC CCA GTT CCT TGG AGT CAG TGG CAG AGG AGT
```

FIGURE 1B
HUMAN HEAVY CHAIN SUBGROUP 1 CONSENSUS [SEQ ID NO 3]

QVQLVQSGAEVKKPGASVKVSCKASGYTFTSYAISWVRQAPGQGLEWM

GWINPGGDTNYAQKFQGRVTITADTSTSTAYMELSSLRSEDTAVYYC

ARPGYGYGGGCYGYWYWGVWGQGTLVTVSS

FIGURE 1C
HEAVY CHAIN V-REGION CODING SEQUENCES OF HUMANIZED B9 "B9HZHC1-0"
[SEQ IDS NOS 4 AND 5]

```
  Q   V   Q   L   V   Q   S   G   A   E   V   K   K   P   G
 CAA GTT CAG CTT GTA CAG TCT GGA GCT GAG GTG AAG AAG CCT GGG      45

A   S   V   K   V   S   C   K   A   S   G   Y   T   F   S
 GCC TCA GTG AAG GTA TCC TGC AAG gCT TCT GGC TAC ACA TTC AGT      90
                                  *
  S   Y   W   I   E   W   V   K   Q   A   P   G   Q   G   L
 AGC TAC TGG ATA GAG TGG GTA AAG CAG GCC CCT GGA CAA GGC CTT     135
              *
  E   W   I   G   E   I   L   P   R   S   G   N   T   N   Y
 GAG TGG ATT GGA GAG ATC TTA CCT AGA AGT GGT AAT ACT AAC TAC     180
                          *   *       *
  N   E   K   F   K   G   K   A   T   F   T   A   D   T   S
 AAT GAG AAG TTC AAG GGC AAG GCC ACA TTC ACT GCA GAT ACA TCC     225

T   S   T   A   Y   M   E   L   S   S   L   R   S   E   D
 ACC AGC ACA GCC TAC ATG GAA CTC AGC AGC CTG AGA TCT GAG GAC     270
                                      *   *
  T   A   V   Y   Y   C   S   S   R   G   V   R   G   S   M
 ACT GCC GTC TAT TAC TGT TCA AGT CGC GGC GTC AGG GGC TCT ATG     315

D   Y   W   G   Q   G   T   L   V   T   V   S   S
 GAC TAC TGG GGT CAA GGA ACC TTA GTC ACC GTC TCC TCA
```

FIGURE 2A
B9 MURINE LIGHT CHAIN V-REGION [SEQ ID NOS 6, 7 AND 39]

```
 D   I   Q   M   T   Q   T   T   S   S   L   S   A   S   L
GAT ATT CAG ATG ACC CAG ACT ACA TCC TCC CTG TCT GCC TCT CTG
CTA TAA GTC TAC TGG GTC TGA TGT AGG AGG GAC AGA CGG AGA GAC

G   D   R   V   T   I   T   C   R   S   S   Q   D   I   S
GGA GAC AGA GTC ACC ATC ACT TGC AGG TCA AGT CAG GAC ATT AGC
CCT CTG TCT CAG TGG TAG TGA ACG TCC AGT TCA GTC CTG TAA TCG

N   F   L   N   W   Y   Q   Q   K   P   D   G   T   V   K
AAT TTT TTA AAC TGG TAT CAG CAG AAA CCA GAT GGA ACT GTT AAA
TTA AAA AAT TTG ACC ATA GTC GTC TTT GGT CTA CCT TGA CAA TTT

L   L   I   Y   Y   T   S   T   L   H   S   G   V   P   S
CTC CTG ATC TAC TAC ACA TCA ACA TTA CAC TCA GGA GTC CCA TCA
GAG GAC TAG ATG ATG TGT AGT TGT AAT GTG AGT CCT CAG GGT AGT

R   F   S   G   S   G   S   G   T   D   Y   S   L   T   I
AGG TTC AGT GGC AGT GGG TCT GGA ACA GAT TAT TCT CTC ACC ATT
TCC AAG TCA CCG TCA CCC AGA CCT TGT CTA ATA AGA GAG TGG TAA

S   N   L   E   Q   E   D   I   A   T   Y   F   C   Q   Q
AGC AAC CTG GAG CAA GAA GAT ATT GCC ACT TAC TTT TGC CAA CAG
TCG TTG GAC CTC GTT CTT CTA TAA CGG TGA ATG AAA ACG GTT GTC

G   N   T   L   P   W   T   F   G   G   G   T   N   L   E
GGT AAT ACG CTT CCT TGG ACG TTC GGT GGA GGC ACC AAC CTG GAA
CCA TTA TGC GAA GGA ACC TGC AAG CCA CCT CCG TGG TTG GAC CTT

I   K   R
ATC AAA CGG
TAG TTT GCC
```

FIGURE 2B
HUMAN VK SUBGROUP I CONSENSUS SEQUENCE [SEQ ID NO 8]

DIQMTQSPSSLSASVGDRVTITCRASQSIVDGSNYLAWYQQKPGKAP

KLLIYASSLESGVPSRFSGSGSGTDFTLTISSLQPEDFATYYCQQYSLP

YWTFGQGTKVEIK

FIGURE 2C
LIGHT CHAIN CODING SEQUENCE OF HUMANIZED B9 "B9HZLC1-0"

```
 D   I   Q   M   T   Q   S   P   S   S   L   S   A   S   V
GAT ATT CAG ATG ACC CAG TCT CCA TCC TCC CTG TCT GCC TCT GTG      45
CTA TAA GTC TAC TGG GTC AGA GGT AGG AGG GAC AGA CGG AGA CAC

G   D   R   V   T   I   T   C   R   S   S   Q   D   I   S
GGA GAC AGA GTC ACC ATC ACT TGC AGG TCA AGT CAG GAC ATT AGC      90
CCT CTG TCT CAG TGG TAG TGA ACG TCC AGT TCA GTC CTG TAA TCG

N   F   L   N   W   Y   Q   Q   K   P   G   K   A   P   K
AAT TTT TTA AAC TGG TAT CAG CAG AAA CCA GGT AAA GCT CCT AAA     135
TTA AAA AAT TTG ACC ATA GTC GTC TTT GGT CCA TTT CGA GGA TTT

L   L   I   Y   Y   T   S   T   L   H   S   G   V   P   S
CTC CTG ATC TAC TAC ACA TCA ACA TTA CAC TCA GGA GTC CCA TCA     180
GAG GAC TAG ATG ATG TGT AGT TGT AAT GTG AGT CCT CAG GGT AGT
                                        *

R   F   S   G   S   G   S   G   T   D   Y   T   L   T   I
AGG TTC AGT GGC AGT GGG TCT GGA ACA GAT TAT ACT CTC ACC ATT     225
TCC AAG TCA CCG TCA CCC AGA CCT TGT CTA ATA TGA GAG TGG TAA

S   S   L   Q   P   E   D   F   A   T   Y   Y   C   Q   Q
AGC AGC CTG CAG CCA GAA GAT TTT GCC ACT TAC TAT TGC CAA CAG     270
TCG TCG GAC GTC GGT CTT CTA AAA CGG TGA ATG ATA ACG GTT GTC

G   N   T   L   P   W   T   F   G   G   G   T
GGT AAT ACG CTT CCT TGG ACG TTC GGT GGA GGT ACC                 306
CCA TTA TGC GAA GGA ACC TGC AAG CCA CCT CCG TGG
```

FIGURE 3
INTERMEDIATE OF SYNTHETIC HEAVY CHAIN [SEQ ID NOS 11, 12 AND 41]

```
AgeI
    T   G   V   H   S   Q   V   Q   L   V   Q   S   G   A   E
    ACC GGT GTC CAC TCC CAA GTT CAG CTT GTA CAG TCT GGA GCT GAG      45
    TGG CCA CAG GTG AGG GTT CAA GTC GAA CAT GTC AGA CCT CGA CTC

V   K   K   P   G   A   S   V   K   V   S   C   K   A   S
    GTG AAG AAG CCT GGG GCC TCA GTG AAG GTA TCC TGC AAG gCT TCT      90
    CAC TTC TTC GGA CCC CGG AGT CAC TTC CAT AGG ACG TTC cGA AGA

G   Y   T   F   S   S   Y   W   I   E   W   V   K   Q   A
    GGC TAC ACA TTC AGT AGC TAC TGG ATA GAG TGG GTA AAG CAG GCC     135
    CCG ATG TGT AAG TCA TCG ATG ACC TAT CTC ACC CAT TTC GTC CGG

BglII
    P   G   Q   G   L   E   W   I   G   E   I   L   P   R   S
    CCT GGA CAA GGC CTT GAG TGG ATT GGA GAG ATC TTA CCT AGA AGT     180
    GGA CCT GTT CCG GAA CTC ACC TAA CCT CTC TAG AAT GGA TCT TCA

G   N   T   N   Y   N   E   K   F   K   G   K   A   T   F
    GGT AAT ACT AAC TAC AAT GAG AAG TTC AAG GGC AAG GCC ACA TTC     225
    CCA TTA TGA TTG ATG TTA CTC TTC AAG TTC CCG TTC CGG TGT AAG

T   A   D   T   S   T   S   T   A   Y   M   E   L   S   S
    ACT GCA GAT ACA TCC ACC AGC ACA GCC TAC ATG GAA CTC AGC AGC     270
    TGA CGT CTA TGT AGG TGG TCG TGT CGG ATG TAC CTT GAG TCG TCG

L   R   S   E   D   T   A   V   Y   Y   C   S   S   R   G
    CTG AGA TCT GAG GAC ACT GCC GTC TAT TAC TGT TCA AGT CGC GGC     315
    GAC TCT AGA CTC CTG TGA CGG CAG ATA ATG ACA AGT TCA GCG CCG

V   R   G   S   M   D   Y   W   G   Q   G   T   L   V   T
    GTC AGG GGC TCT ATG GAC TAC TGG GGT CAA GGA ACC TTA GTC ACC     360
    CAG TCC CCG AGA TAC CTG ATG ACC CCA GTT CCT TGG AAT CAG TGG

ApaI
    V   S   S   A   S   T   K   G
    GTC TCC TCA GCT AGT ACC AAG GGC CC                              386
    CAG AGG AGT CGA TCA TGG TTC CCG GG
```

FIGURE 4
INTERMEDIATE OF SYNTHETIC LIGHT CHAIN [SEQ ID NOS 13, 14 AND 42]

```
    AgeI
    A   T   G   V   H   S   D   I   Q   M   T   Q   S   P   S
    GCT ACC GGT GTC CAC TCC GAT ATT CAG ATG ACC CAG TCT CCA TCC      45
    CGA TGG CCA CAG GTG AGG CTA TAA GTC TAC TGG GTC AGA GGT AGG

S   L   S   A   S   V   G   D   R   V   T   I   T   C   R
    TCC CTG TCT GCC TCT GTG GGA GAC AGA GTC ACC ATC ACT TGC AGG      90
    AGG GAC AGA CGG AGA CAC CCT CTG TCT CAG TGG TAG TGA ACG TCC

S   S   Q   D   I   S   N   F   L   N   W   Y   Q   Q   K
    TCA AGT CAG GAC ATT AGC AAT TTT TTA AAC TGG TAT CAG CAG AAA     135
    AGT TCA GTC CTG TAA TCG TTA AAA AAT TTG ACC ATA GTC GTC TTT

HinDIII
    P   G   K   A   P   K   L   L   I   Y   Y   T   S   T   L
    CCA GGT AAA GCT CCT AAG CTT CTG ATC TAC TAC ACA TCA ACA TTA     180
    GGT CCA TTT CGA GGA TTC GAA GAC TAG ATG ATG TGT AGT TGT AAT

H   S   G   V   P   S   R   F   S   G   S   G   S   G   T
    CAC TCA GGA GTC CCA TCA AGG TTC AGT GGC AGT GGG TCT GGA ACA     225
    GTG AGT CCT CAG GGT AGT TCC AAG TCA CCG TCA CCC AGA CCT TGT

D   Y   T   L   T   I   S   S   L   Q   P   E   D   F   A
    GAT TAT ACT CTC ACC ATT AGC AGC CTG CAG CCA GAA GAT TTT GCC     270
    CTA ATA TGA GAG TGG TAA TCG TCG GAC GTC GGT CTT CTA AAA CGG

T   Y   Y   C   Q   Q   G   N   T   L   P   W   T   F   G
    ACT TAC TAT TGC CAA CAG GGT AAT ACG CTT CCT TGG ACG TTC GGT     315
    TGA ATG ATA ACG GTT GTC CCA TTA TGC GAA GGA ACC TGC AAG CCA

KpnI
    G   G   T
    GGA GGT ACC                                                     324
    CCT CCA TGG
```

FIGURE 5

MODIFIED HUMAN REI KAPPA CHAIN V REGION [SEQ ID NO 15]

DIQMTQSPSS LSASVGDRVT ITCQASQDII KYLNWYQQKP GKAPKLLIYE

ASNLQAGVPS RFSGSGSGTD FTFTISSLQP EDIATYYCQQ

FIGURE 6
LIGHT CHAIN ENCODING SEQUENCE OF HUMANIZED B9 "B9HZLCREI"

```
  D   I   Q   M   T   Q   S   P   S   S   L   S   A   A   V
GAT ATT CAG ATG ACC CAG TCT CCA TCC TCC CTG TCT GCC TCT GTG    45
CTA TAA GTC TAC TGG GTC AGA GGT AGG AGG GAC AGA CGG AGA CAC

G   D   R   V   T   I   T   C   R   S   S   Q   D   I   S
GGA GAC AGA GTC ACC ATC ACT TGC AGG TCA AGT CAG GAC ATT AGC    90
CCT CTG TCT CAG TGG TAG TGA ACG TCC AGT TCA GTC CTG TAA TCG

N   F   L   N   W   Y   Q   Q   K   P   G   K   A   P   K
AAT TTT TTA AAC TGG TAT CAG CAG AAA CCA GGT AAA GCT CCT AAA   135
TTA AAA AAT TTG ACC ATA GTC GTC TTT GGT CCA TTT CGA GGA TTT

L   L   I   Y   Y   T   S   T   L   H   S   G   V   P   S
CTC CTG ATC TAC TAC ACA TCA ACA TTA CAC TCA GGA GTC CCA TCA   180
GAG GAC TAG ATG ATG TGT AGT TGT AAT GTG AGT CCT CAG GGT AGT

*
  R   F   S   G   S   G   S   G   T   D   Y   T   F   T   I
AGG TTC AGT GGC AGT GGG TCT GGA ACA GAT TAT ACT TTC ACC ATT   225
TCC AAG TCA CCG TCA CCC AGA CCT TGT CTA ATA TGA AAG TGG TAA

S   S   L   Q   P   E   D   I   A   T   Y   Y   C   Q   Q
AGC AGC CTG CAG CCA GAA GAT ATT GCC ACT TAC TAT TGC CAA CAG   270
TCG TCG GAC GTC GGT CTT CTA TAA CGG TGA ATG ATA ACG GTT GTC

G   N   T   L   P   W   T   F   G   G   G   T
GGT AAT ACG CTT CCT TGG ACG TTC GGT GGA GGT ACC                306
CCA TTA TGC GAA GGA ACC TGC AAG CCA CCT CCA TGG
```

FIGURE 7
LIGHT CHAIN ENCODING SEQUENCE OF HUMANIZED B9 "B9HZLC1-1"

```
  D   I   Q   M   T   Q   S   P   S   S   L   S   A   A   V
 GAT ATT CAG ATG ACC CAG TCT CCA TCC TCC CTG TCT GCC TCT GTG       45
 CTA TAA GTC TAC TGG GTC AGA GGT AGG AGG GAC AGA CGG AGA CAC

G   D   R   V   T   I   T   C   R   S   S   Q   D   I   S
 GGA GAC AGA GTC ACC ATC ACT TGC AGG TCA AGT CAG GAC ATT AGC       90
 CCT CTG TCT CAG TGG TAG TGA ACG TCC AGT TCA GTC CTG TAA TCG

N   F   L   N   W   Y   Q   Q   K   P   G   K   A   P   K
 AAT TTT TTA AAC TGG TAT CAG CAG AAA CCA GGT AAA GCT CCT AAA      135
 TTA AAA AAT TTG ACC ATA GTC GTC TTT GGT CCA TTT CGA GGA TTT

L   L   I   Y   Y   T   S   T   L   H   S   G   V   P   S
 CTC CTG ATC TAC TAC ACA TCA ACA TTA CAC TCA GGA GTC CCA TCA      180
 GAG GAC TAG ATG ATG TGT AGT TGT AAT GTG AGT CCT CAG GGT AGT

*
  R   F   S   G   S   G   S   G   T   D   Y   T   L   T   I
 AGG TTC AGT GGC AGT GGG TCT GGA ACA GAT TAT ACT CTC ACC ATT      225
 TCC AAG TCA CCG TCA CCC AGA CCT TGT CTA ATA TGA GAG TGG TAA

S   S   L   Q   P   E   D   F   A   T   Y   Y   C   Q   Q
 AGC AGC CTG CAG CCA GAA GAT TTT GCC ACT TAC TAT TGC CAA CAG      270
 TCG TCG GAC GTC GGT CTT CTA AAA CGG TGA ATG ATA ACG GTT GTC

*
  G   N   T   L   P   W   T   F   G   G   G   T   N   V   E
 GGT AAT ACG CTT CCT TGG ACG TTC GGT GGA GGT ACC AAT GTG GAA      315
 CCA TTA TGC GAA GGA ACC TGC AAG CCA CCT CCA TGG TTA CAC CTT
```

Mean weight (n= 8) of tumor in HT-29 derived tumors, injected I.P.

Mean weight (n= 8) of tumor in HT-29 derived tumors, injected Sub-cutaneously

SEQUENCE LISTING

<160> NUMBER OF SEQ ID NOS: 37

<210> SEQ ID NO 1
<211> LENGTH: 354
<212> TYPE: DNA
<213> ORGANISM: Mus Musculus
<220> FEATURE:
<221> NAME/KEY: CDS -continued

<222> LOCATION: (1)...(354)

<400> SEQUENCE: 1

```
caa gtt cag ctt caa cag tct gga gct gag ctg atg aag cct ggg gcc     48
Gln Val Gln Leu Gln Gln Ser Gly Ala Glu Leu Met Lys Pro Gly Ala
 1               5                  10                  15 tca gtg aag ata tcc tgc aag gct act ggc tac aca ttc agt agc tac     96
Ser Val Lys Ile Ser Cys Lys Ala Thr Gly Tyr Thr Phe Ser Ser Tyr
             20                  25                  30 tgg ata gag tgg gta aag cag agg cct gga cat ggc ctt gag tgg att    144
Trp Ile Glu Trp Val Lys Gln Arg Pro Gly His Gly Leu Glu Trp Ile
         35                  40                  45 gga gag att tta cct aga agt ggt aat act aac tac aat gag aag ttc    192
Gly Glu Ile Leu Pro Arg Ser Gly Asn Thr Asn Tyr Asn Glu Lys Phe
     50                  55                  60 aag ggc aag gcc aca ttc act gca gaa aca tcc tcc aac aca gcc tac    240
Lys Gly Lys Ala Thr Phe Thr Ala Glu Thr Ser Ser Asn Thr Ala Tyr
 65                  70                  75                  80 atg caa ctc agc agc ctg aca cct gag gac tct gcc gtc tat tac tgt    288
Met Gln Leu Ser Ser Leu Thr Pro Glu Asp Ser Ala Val Tyr Tyr Cys
                 85                  90                  95 tca agt cgc ggc gtc agg ggc tct atg gac tac tgg ggt caa gga acc    336
Ser Ser Arg Gly Val Arg Gly Ser Met Asp Tyr Trp Gly Gln Gly Thr
            100                 105                 110 tca gtc acc gtc tcc tca                                            354
Ser Val Thr Val Ser Ser
        115
```

<210> SEQ ID NO 2
<211> LENGTH: 118
<212> TYPE: PRT
<213> ORGANISM: Mus Musculus

<400> SEQUENCE: 2

```
Gln Val Gln Leu Gln Gln Ser Gly Ala Glu Leu Met Lys Pro Gly Ala
 1               5                  10                  15

Ser Val Lys Ile Ser Cys Lys Ala Thr Gly Tyr Thr Phe Ser Ser Tyr
             20                  25                  30

Trp Ile Glu Trp Val Lys Gln Arg Pro Gly His Gly Leu Glu Trp Ile
         35                  40                  45

Gly Glu Ile Leu Pro Arg Ser Gly Asn Thr Asn Tyr Asn Glu Lys Phe
     50                  55                  60

Lys Gly Lys Ala Thr Phe Thr Ala Glu Thr Ser Ser Asn Thr Ala Tyr
 65                  70                  75                  80

Met Gln Leu Ser Ser Leu Thr Pro Glu Asp Ser Ala Val Tyr Tyr Cys
                 85                  90                  95

Ser Ser Arg Gly Val Arg Gly Ser Met Asp Tyr Trp Gly Gln Gly Thr
            100                 105                 110

Ser Val Thr Val Ser Ser
        115
```

<210> SEQ ID NO 3
<211> LENGTH: 125
<212> TYPE: PRT
<213> ORGANISM: Homo sapiens

<400> SEQUENCE: 3

```
Gln Val Gln Leu Val Gln Ser Gly Ala Glu Val Lys Lys Pro Gly Ala
 1               5                  10                  15
```

```
Ser Val Lys Val Ser Cys Lys Ala Ser Gly Tyr Thr Phe Thr Ser Tyr
            20                  25                  30

Ala Ile Ser Trp Val Arg Gln Ala Pro Gly Gln Gly Leu Glu Trp Met
            35                  40                  45

Gly Trp Ile Asn Pro Gly Asp Thr Asn Tyr Ala Gln Lys Phe Gln
 50                  55                  60

Gly Arg Val Thr Ile Thr Ala Asp Thr Ser Ser Thr Ala Tyr Met
 65                  70                  75                  80

Glu Leu Ser Ser Leu Arg Ser Glu Asp Thr Ala Val Tyr Tyr Cys Ala
            85                  90                  95

Arg Pro Gly Tyr Gly Tyr Gly Gly Cys Tyr Gly Tyr Trp Tyr Trp
                 100                 105                 110

Gly Val Trp Gly Gln Gly Thr Leu Val Thr Val Ser Ser
            115                 120                 125

<210> SEQ ID NO 4
<211> LENGTH: 354
<212> TYPE: DNA
<213> ORGANISM: Artificial Sequence
<220> FEATURE:
<221> NAME/KEY: CDS
<222> LOCATION: (1)...(354)
<223> OTHER INFORMATION: Wherein the nucleotides represent the synthetic
      heavy chain variable region of the consensus,
      humanized heavy chain B9HZHC 1-0

<400> SEQUENCE: 4 caa gtt cag ctt gta cag tct gga gct gag gtg aag aag cct ggg gcc         48
Gln Val Gln Leu Val Gln Ser Gly Ala Glu Val Lys Lys Pro Gly Ala
 1               5                  10                  15 tca gtg aag gta tcc tgc aag gct tct ggc tac aca ttc agt agc tac         96
Ser Val Lys Val Ser Cys Lys Ala Ser Gly Tyr Thr Phe Ser Ser Tyr
            20                  25                  30 tgg ata gag tgg gta aag cag gcc cct gga caa ggc ctt gag tgg att       144
Trp Ile Glu Trp Val Lys Gln Ala Pro Gly Gln Gly Leu Glu Trp Ile
        35                      40                  45 gga gag atc tta cct aga agt ggt aat act aac tac aat gag aag ttc       192
Gly Glu Ile Leu Pro Arg Ser Gly Asn Thr Asn Tyr Asn Glu Lys Phe
 50                  55                  60 aag ggc aag gcc aca ttc act gca gat aca tcc acc agc aca gcc tac       240
Lys Gly Lys Ala Thr Phe Thr Ala Asp Thr Ser Thr Ser Thr Ala Tyr
 65                  70                  75                  80 atg gaa ctc agc agc ctg aga tct gag gac act gcc gtc tat tac tgt       288
Met Glu Leu Ser Ser Leu Arg Ser Glu Asp Thr Ala Val Tyr Tyr Cys
            85                  90                  95 tca agt cgc ggc gtc agg ggc tct atg gac tac tgg ggt caa gga acc       336
Ser Ser Arg Gly Val Arg Gly Ser Met Asp Tyr Trp Gly Gln Gly Thr
                 100                 105                 110 tta gtc acc gtc tcc tca                                                354
Leu Val Thr Val Ser Ser
            115

<210> SEQ ID NO 5
<211> LENGTH: 118
<212> TYPE: PRT
<213> ORGANISM: Artificial Sequence
<220> FEATURE:
<223> OTHER INFORMATION: Wherein the amino acids represent the synthetic
      heavy chain variable region of the consensus,
      humanized heavy chain B9HZHC 1-0

<400> SEQUENCE: 5
```

```
Gln Val Gln Leu Val Gln Ser Gly Ala Glu Val Lys Lys Pro Gly Ala
  1               5                  10                  15
Ser Val Lys Val Ser Cys Lys Ala Ser Gly Tyr Thr Phe Ser Ser Tyr
             20                  25                  30
Trp Ile Glu Trp Val Lys Gln Ala Pro Gly Gln Gly Leu Glu Trp Ile
         35                  40                  45
Gly Glu Ile Leu Pro Arg Ser Gly Asn Thr Asn Tyr Asn Glu Lys Phe
     50                  55                  60
Lys Gly Lys Ala Thr Phe Thr Ala Asp Thr Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ser Ser Arg Gly Val Arg Gly Ser Met Asp Tyr Trp Gly Gln Gly Thr
                100                 105                 110
Leu Val Thr Val Ser Ser
            115
```

```
<210> SEQ ID NO 6
<211> LENGTH: 324
<212> TYPE: DNA
<213> ORGANISM: Mus Musculus
<220> FEATURE:
<221> NAME/KEY: CDS
<222> LOCATION: (1)...(324)

<400> SEQUENCE: 6 gat att cag atg acc cag act aca tcc tcc ctg tct gcc tct ctg gga      48
Asp Ile Gln Met Thr Gln Thr Thr Ser Ser Leu Ser Ala Ser Leu Gly
  1               5                  10                  15 gac aga gtc acc atc act tgc agg tca agt cag gac att agc aat ttt      96
Asp Arg Val Thr Ile Thr Cys Arg Ser Ser Gln Asp Ile Ser Asn Phe
             20                  25                  30 tta aac tgg tat cag cag aaa cca gat gga act gtt aaa ctc ctg atc     144
Leu Asn Trp Tyr Gln Gln Lys Pro Asp Gly Thr Val Lys Leu Leu Ile
         35                  40                  45 tac tac aca tca aca tta cac tca gga gtc cca tca agg ttc agt ggc     192
Tyr Tyr Thr Ser Thr Leu His Ser Gly Val Pro Ser Arg Phe Ser Gly
     50                  55                  60 agt ggg tct gga aca gat tat tct ctc acc att agc aac ctg gag caa     240
Ser Gly Ser Gly Thr Asp Tyr Ser Leu Thr Ile Ser Asn Leu Glu Gln
 65                  70                  75                  80 gaa gat att gcc act tac ttt tgc caa cag ggt aat acg ctt cct tgg     288
Glu Asp Ile Ala Thr Tyr Phe Cys Gln Gln Gly Asn Thr Leu Pro Trp
                 85                  90                  95 acg ttc ggt gga ggc acc aac ctg gaa atc aaa cgg                     324
Thr Phe Gly Gly Gly Thr Asn Leu Glu Ile Lys Arg
                100                 105
```

```
<210> SEQ ID NO 7
<211> LENGTH: 108
<212> TYPE: PRT
<213> ORGANISM: Mus Musculus

<400> SEQUENCE: 7

Asp Ile Gln Met Thr Gln Thr Thr Ser Ser Leu Ser Ala Ser Leu Gly
  1               5                  10                  15

Asp Arg Val Thr Ile Thr Cys Arg Ser Ser Gln Asp Ile Ser Asn Phe
             20                  25                  30

Leu Asn Trp Tyr Gln Gln Lys Pro Asp Gly Thr Val Lys Leu Leu Ile
         35                  40                  45

Tyr Tyr Thr Ser Thr Leu His Ser Gly Val Pro Ser Arg Phe Ser Gly
```

```
                                50                       55                       60
Ser Gly Ser Gly Thr Asp Tyr Ser Leu Thr Ile Ser Asn Leu Glu Gln
 65                      70                       75                       80

Glu Asp Ile Ala Thr Tyr Phe Cys Gln Gln Gly Asn Thr Leu Pro Trp
                         85                       90                       95

Thr Phe Gly Gly Gly Thr Asn Leu Glu Ile Lys Arg
                    100                      105

<210> SEQ ID NO 8
<211> LENGTH: 109
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
 1               5                       10                       15

Asp Arg Val Thr Ile Thr Cys Arg Ala Ser Gln Ser Ile Val Asp Gly
                20                       25                       30

Ser Asn Tyr Leu Ala Trp Tyr Gln Gln Lys Pro Gly Lys Ala Pro Lys
            35                       40                       45

Leu Leu Ile Tyr Ala Ser Ser Leu Glu Ser Gly Val Pro Ser Arg Phe
 50                      55                       60

Ser Gly Ser Gly Ser Gly Thr Asp Phe Thr Leu Thr Ile Ser Ser Leu
 65                      70                       75                       80

Gln Pro Glu Asp Phe Ala Thr Tyr Tyr Cys Gln Gln Tyr Ser Leu Pro
                         85                       90                       95

Tyr Trp Thr Phe Gly Gln Gly Thr Lys Val Glu Ile Lys
                    100                      105

<210> SEQ ID NO 9
<211> LENGTH: 307
<212> TYPE: DNA
<213> ORGANISM: Artificial Sequence
<220> FEATURE:
<221> NAME/KEY: CDS
<222> LOCATION: (1)...(306)
<223> OTHER INFORMATION: Wherein the nucleotides represent the synthetic
      heavy chain variable region of the consensus,
      humanized light chain B9HZHC 1-0

<400> SEQUENCE: 9 gat att cag atg acc cag tct cca tcc tcc ctg tct gcc tct gtg gga       48
Asp Ile Gln Met Thr Gln Ser Pro Ser Ser Leu Ser Ala Ser Val Gly
 1               5                       10                       15 gac aga gtc acc atc act tgc agg tca agt cag gac att agc aat ttt       96
Asp Arg Val Thr Ile Thr Cys Arg Ser Ser Gln Asp Ile Ser Asn Phe
                20                       25                       30 tta aac tgg tat cag cag aaa cca ggt aaa gct cct aaa ctc ctg atc      144
Leu Asn Trp Tyr Gln Gln Lys Pro Gly Lys Ala Pro Lys Leu Leu Ile
            35                       40                       45 tac tac aca tca aca tta cac tca gga gtc cca tca agg ttc agt ggc      192
Tyr Tyr Thr Ser Thr Leu His Ser Gly Val Pro Ser Arg Phe Ser Gly
 50                      55                       60 agt ggg tct gga aca gat tat act ctc acc att agc agc ctg cag cca      240
Ser Gly Ser Gly Thr Asp Tyr Thr Leu Thr Ile Ser Ser Leu Gln Pro
 65                      70                       75                       80 gaa gat ttt gcc act tac tat tgc caa cag ggt aat acg gct tcc ttg      288
Glu Asp Phe Ala Thr Tyr Tyr Cys Gln Gln Gly Asn Thr Ala Ser Leu
                         85                       90                       95 gac gtt cgg tgg agg tac c                                            307
```

```
Asp Val Arg Trp Arg Tyr
            100

<210> SEQ ID NO 10
<211> LENGTH: 102
<212> TYPE: PRT
<213> ORGANISM: Artificial Sequence
<220> FEATURE:
<223> OTHER INFORMATION: Wherein the amino acids represent the synthetic
      light chain variable region of the consensus,
      humanized light chain B9HZHC 1-0

<400> SEQUENCE: 10

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Asp Ile Ser Asn Phe
                20                  25                  30

Leu Asn Trp Tyr Gln Gln Lys Pro Gly Lys Ala Pro Lys Leu Leu Ile
            35                  40                  45

Tyr Tyr Thr Ser Thr Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Ala Ser Leu
                85                  90                  95

Asp Val Arg Trp Arg Tyr
            100

<210> SEQ ID NO 11
<211> LENGTH: 386
<212> TYPE: DNA
<213> ORGANISM: Artificial Sequence
<220> FEATURE:
<221> NAME/KEY: CDS
<222> LOCATION: (1)...(384)
<223> OTHER INFORMATION: Wherein the nucleotides represent the
      intermediate of the synthetic B9 heavy chain variable region

<400> SEQUENCE: 11 acc ggt gtc cac tcc caa gtt cag ctt gta cag tct gga gct gag gtg     48
Thr Gly Val His Ser Gln Val Gln Leu Val Gln Ser Gly Ala Glu Val
 1               5                  10                  15 aag aag cct ggg gcc tca gtg aag gta tcc tgc aag gct tct ggc tac     96
Lys Lys Pro Gly Ala Ser Val Lys Val Ser Cys Lys Ala Ser Gly Tyr
                20                  25                  30 aca ttc agt agc tac tgg ata gag tgg gta aag cag gcc cct gga caa    144
Thr Phe Ser Ser Tyr Trp Ile Glu Trp Val Lys Gln Ala Pro Gly Gln
            35                  40                  45 ggc ctt gag tgg att gga gag atc tta cct aga agt ggt aat act aac    192
Gly Leu Glu Trp Ile Gly Glu Ile Leu Pro Arg Ser Gly Asn Thr Asn
        50                  55                  60 tac aat gag aag ttc aag ggc aag gcc aca ttc act gca gat aca tcc    240
Tyr Asn Glu Lys Phe Lys Gly Lys Ala Thr Phe Thr Ala Asp Thr Ser
65                  70                  75                  80 acc agc aca gcc tac atg gaa ctc agc agc ctg aga tct gag gac act    288
Thr Ser Thr Ala Tyr Met Glu Leu Ser Ser Leu Arg Ser Glu Asp Thr
                85                  90                  95 gcc gtc tat tac tgt tca agt cgc ggc gtc agg ggc tct atg gac tac    336
Ala Val Tyr Tyr Cys Ser Ser Arg Gly Val Arg Gly Ser Met Asp Tyr
            100                 105                 110 tgg ggt caa gga acc tta gtc acc gtc tcc tca gct agt acc aag ggc    384
Trp Gly Gln Gly Thr Leu Val Thr Val Ser Ser Ala Ser Thr Lys Gly
```

```
                  115                 120                 125
cc                                                                      386

<210> SEQ ID NO 12
<211> LENGTH: 128
<212> TYPE: PRT
<213> ORGANISM: Artificial Sequence
<220> FEATURE:
<223> OTHER INFORMATION: Wherein the amino acids represent the
      intermediate of the synthetic B9 heavy chain variable region

<400> SEQUENCE: 12

Thr Gly Val His Ser Gln Val Gln Leu Val Gln Ser Gly Ala Glu Val
 1               5                  10                  15

Lys Lys Pro Gly Ala Ser Val Lys Val Ser Cys Lys Ala Ser Gly Tyr
            20                  25                  30

Thr Phe Ser Ser Tyr Trp Ile Glu Trp Val Lys Gln Ala Pro Gly Gln
        35                  40                  45

Gly Leu Glu Trp Ile Gly Glu Ile Leu Pro Arg Ser Gly Asn Thr Asn
    50                  55                  60

Tyr Asn Glu Lys Phe Lys Gly Lys Ala Thr Phe Thr Ala Asp Thr Ser
65                  70                  75                  80

Thr Ser Thr Ala Tyr Met Glu Leu Ser Ser Leu Arg Ser Glu Asp Thr
                85                  90                  95

Ala Val Tyr Tyr Cys Ser Ser Arg Gly Val Arg Gly Ser Met Asp Tyr
            100                 105                 110

Trp Gly Gln Gly Thr Leu Val Thr Val Ser Ser Ala Ser Thr Lys Gly
        115                 120                 125

<210> SEQ ID NO 13
<211> LENGTH: 324
<212> TYPE: DNA
<213> ORGANISM: Artificial Sequence
<220> FEATURE:
<223> OTHER INFORMATION: Wherein the nucleotides represent the
      intermediate of the synthetic B9 murine light chain variable
      region

<400> SEQUENCE: 13
gctaccggtg tccactccga tattcagatg acccagtctc catcctccct gtctgcctct      60
gtgggagaca gagtcaccat cacttgcagg tcaagtcagg acattagcaa ttttttaaac     120
tggtatcagc agaaaccagg taaagctcct aagcttctga tctactacac atcaacatta     180
cactcaggag tcccatcaag gttcagtggc agtgggtctg gaacagatta tactctcacc     240
attagcagcc tgcagccaga agattttgcc acttactatt gccaacaggg taatacgctt     300
ccttggacgt tcggtggagg tacc                                            324

<210> SEQ ID NO 14
<211> LENGTH: 108
<212> TYPE: PRT
<213> ORGANISM: Artificial Sequence
<220> FEATURE:
<223> OTHER INFORMATION: Wherein the amino acid sequences represent the
      intermediate of the synthetic B9 murine light
      chain variable region

<400> SEQUENCE: 14

Ala Thr Gly Val His Ser Asp Ile Gln Met Thr Gln Ser Pro Ser Ser
 1               5                  10                  15

Leu Ser Ala Ser Val Gly Asp Arg Val Thr Ile Thr Cys Arg Ser Ser
```

```
                       20                  25                  30
Gln Asp Ile Ser Asn Phe Leu Asn Trp Tyr Gln Gln Lys Pro Gly Lys
                35                  40                  45

Ala Pro Lys Leu Leu Ile Tyr Tyr Thr Ser Thr Leu His Ser Gly Val
 50                  55                  60

Pro Ser Arg Phe Ser Gly Ser Gly Ser Gly Thr Asp Tyr Thr Leu Thr
 65                  70                  75                  80

Ile Ser Ser Leu Gln Pro Glu Asp Phe Ala Thr Tyr Tyr Cys Gln Gln
                 85                  90                  95

Gly Asn Thr Leu Pro Trp Thr Phe Gly Gly Gly Thr
                100                 105

<210> SEQ ID NO 15
<211> LENGTH: 90
<212> TYPE: PRT
<213> ORGANISM: Artificial Sequence
<220> FEATURE:
<223> OTHER INFORMATION: Wherein the amino acid sequence represents a
      modified human REI kappa Variable region

<400> SEQUENCE: 15

Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Ile Lys Tyr
                20                  25                  30

Leu Asn Trp Tyr Gln Gln Lys Pro Gly Lys Ala Pro Lys Leu Leu Ile
                35                  40                  45

Tyr Glu Ala Ser Asn Leu Gln Ala Gly Val Pro Ser Arg Phe Ser Gly
 50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln
                85                  90

<210> SEQ ID NO 16
<211> LENGTH: 16
<212> TYPE: PRT
<213> ORGANISM: Mus musculus
<220> FEATURE:

<400> SEQUENCE: 16

Gln Val Gln Leu Gln Gln Ser Gly Ala Glu Leu Met Lys Pro Gly Ala
 1               5                  10                  15

<210> SEQ ID NO 17
<211> LENGTH: 15
<212> TYPE: PRT
<213> ORGANISM: Mus musculus
<220> FEATURE:
<221> NAME/KEY: unsure
<222> LOCATION: (12)(14)
<223> OTHER INFORMATION: Where Xaa can represent any one of the naturally
      occurring amino
<223> OTHER INFORMATION: acids

<400> SEQUENCE: 17

Asp Ile Gln Met Thr Gln Thr Thr Ser Ser Leu Xaa Ala Xaa Leu
 1               5                  10                  15

<210> SEQ ID NO 18
<211> LENGTH: 18
<212> TYPE: DNA
```

<213> ORGANISM: Mus musculus

<400> SEQUENCE: 18
aggggccagt ggatagac                                                        18

<210> SEQ ID NO 19
<211> LENGTH: 35
<212> TYPE: DNA
<213> ORGANISM: Mus musculus
<220> FEATURE:
<221> NAME/KEY: unsure
<222> LOCATION: (24)(30)
<223> OTHER INFORMATION: Where n can equal a,c,t, or g

<400> SEQUENCE: 19
gctaccggtg tccactccca agtncarctn carca                                     35

<210> SEQ ID NO 20
<211> LENGTH: 21
<212> TYPE: DNA
<213> ORGANISM: Mus musculus

<400> SEQUENCE: 20
gcacctccag atgttaactg c                                                    21

<210> SEQ ID NO 21
<211> LENGTH: 35
<212> TYPE: DNA
<213> ORGANISM: Mus musculus
<220> FEATURE:
<221> NAME/KEY: unsure
<222> LOCATION: (33)
<223> OTHER INFORMATION: Where n can equal a,c,t, or g

<400> SEQUENCE: 21
gctaccggtg tccactccga yathcaratg acnca                                     35

<210> SEQ ID NO 22
<211> LENGTH: 96
<212> TYPE: DNA
<213> ORGANISM: Artificial Sequence
<220> FEATURE:
<223> OTHER INFORMATION: Wherein the nucleotides represent synthetic
      humanized light chain variable region designed
      using human light chain subgroup I consensus
      sequence framework

<400> SEQUENCE: 22
tttttggcta ccggtgtcca ctccgatatt cagatgaccc agtctccatc ctccctgtct          60
gcctctgtgg gagacagagt caccatcact tgcagg                                    96

<210> SEQ ID NO 23
<211> LENGTH: 114
<212> TYPE: DNA
<213> ORGANISM: Artificial Sequence
<220> FEATURE:
<223> OTHER INFORMATION: Wherein the nucleotides represent synthetic
      humanized light chain variable region designed
      using human light chain subgroup I consensus
      sequence frameworks

<400> SEQUENCE: 23
taatgttgat gtgtagtaga tcagaagctt aggagcttta cctggtttct gctgatacca          60
gtttaaaaaa ttgctaatgt cctgacttga cctgcaagtg atggtgactc tgtc               114

```
<210> SEQ ID NO 24
<211> LENGTH: 99
<212> TYPE: DNA
<213> ORGANISM: Artificial Sequence
<220> FEATURE:
<223> OTHER INFORMATION: Wherein the nucleotides represent synthetic
      humanized light chain variable region designed
      using human light chain subgroup I consensus
      sequence frameworks

<400> SEQUENCE: 24
ctgatctact acacatcaac attacactca ggagtcccat caaggttcag tggcagtggg      60
tctggaacag attatactct caccattagc agcctgcag                             99

<210> SEQ ID NO 25
<211> LENGTH: 96
<212> TYPE: DNA
<213> ORGANISM: Artificial Sequence
<220> FEATURE:
<223> OTHER INFORMATION: Wherein the nucleotides represent synthetic
      humanized light chain variable region designed
      using human light chain subgroup I consensus
      sequence frameworks

<400> SEQUENCE: 25
tgtacgggta cctccaccga acgtccaagg aagcgtatta ccctgttggc aatagtaagt      60
ggcaaaatct tctggctgca ggctgctaat ggtgag                                96

<210> SEQ ID NO 26
<211> LENGTH: 33
<212> TYPE: DNA
<213> ORGANISM: Artificial Sequence
<220> FEATURE:
<223> OTHER INFORMATION: Wherein  the nucleotides represent a primer used
      to PCT amplify the synthetic Vk region

<400> SEQUENCE: 26
tttttggcta ccggtgtcca ctccgatatt cag                                   33

<210> SEQ ID NO 27
<211> LENGTH: 27
<212> TYPE: DNA
<213> ORGANISM: Artificial Sequence
<220> FEATURE:
<223> OTHER INFORMATION: Wherein the nucleotides represent primers used
      to PCR amplify the synthetic Vk region

<400> SEQUENCE: 27
acgggtacct ccaccgaacg tccaagg                                          27

<210> SEQ ID NO 28
<211> LENGTH: 306
<212> TYPE: DNA
<213> ORGANISM: Artificial Sequence
<220> FEATURE:
<221> NAME/KEY: CDS
<222> LOCATION: (1)...(306)
<223> OTHER INFORMATION: Wherein the nucleotides represent a light chain
      encoding sequence of humanized B9 AB9HZLCREI

<400> SEQUENCE: 28 gat att cag atg acc cag tct cca tcc tcc ctg tct gcc tct gtg gga        48
Asp Ile Gln Met Thr Gln Ser Pro Ser Ser Leu Ser Ala Ser Val Gly
 1               5                  10                  15 gac aga gtc acc atc act tgc agg tca agt cag gac att agc aat ttt        96
Asp Arg Val Thr Ile Thr Cys Arg Ser Ser Gln Asp Ile Ser Asn Phe
            20                  25                  30
```

```
tta aac tgg tat cag cag aaa cca ggt aaa gct cct aaa ctc ctg atc    144
Leu Asn Trp Tyr Gln Gln Lys Pro Gly Lys Ala Pro Lys Leu Leu Ile
        35                  40                  45 tac tac aca tca aca tta cac tca gga gtc cca tca agg ttc agt ggc    192
Tyr Tyr Thr Ser Thr Leu His Ser Gly Val Pro Ser Arg Phe Ser Gly
 50                  55                  60 agt ggg tct gga aca gat tat act ttc acc att agc agc ctg cag cca    240
Ser Gly Ser Gly Thr Asp Tyr Thr Phe Thr Ile Ser Ser Leu Gln Pro
 65                  70                  75                  80 gaa gat att gcc act tac tat tgc caa cag ggt aat acg ctt cct tgg    288
Glu Asp Ile Ala Thr Tyr Tyr Cys Gln Gln Gly Asn Thr Leu Pro Trp
                 85                  90                  95 acg ttc ggt gga ggt acc                                            306
Thr Phe Gly Gly Gly Thr
            100
```

<210> SEQ ID NO 29
<211> LENGTH: 102
<212> TYPE: PRT
<213> ORGANISM: Artificial Sequence
<220> FEATURE:
<223> OTHER INFORMATION: Wherein the amino acids represent a light chain
      encoding sequence of humanized B9 AB9HZLCREI

<400> SEQUENCE: 29

Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Asp Ile Ser Asn Phe
             20                  25                  30

Leu Asn Trp Tyr Gln Gln Lys Pro Gly Lys Ala Pro Lys Leu Leu Ile
         35                  40                  45

Tyr Tyr Thr Ser Thr Leu His Ser Gly Val Pro Ser Arg Phe Ser Gly
 50                  55                  60

Ser Gly Ser Gly Thr Asp Tyr Thr Phe Thr Ile Ser Ser Leu Gln Pro
65                   70                  75                  80

Glu Asp Ile Ala Thr Tyr Tyr Cys Gln Gln Gly Asn Thr Leu Pro Trp
                 85                  90                  95

Thr Phe Gly Gly Gly Thr
            100

<210> SEQ ID NO 30
<211> LENGTH: 315
<212> TYPE: DNA
<213> ORGANISM: Artificial Sequence
<220> FEATURE:
<221> NAME/KEY: CDS
<222> LOCATION: (1)...(315)
<223> OTHER INFORMATION: Wherein the nucleotides represent the light
      chain encoding sequence of the humanized B9, AB9HZLC1-1

<400> SEQUENCE: 30

```
gat att cag atg acc cag tct cca tcc tcc ctg tct gcc tct gtg gga    48
Asp Ile Gln Met Thr Gln Ser Pro Ser Ser Leu Ser Ala Ser Val Gly
 1               5                  10                  15 gac aga gtc acc atc act tgc agg tca agt cag gac att agc aat ttt    96
Asp Arg Val Thr Ile Thr Cys Arg Ser Ser Gln Asp Ile Ser Asn Phe
             20                  25                  30 tta aac tgg tat cag cag aaa cca ggt aaa gct cct aaa ctc ctg atc    144
Leu Asn Trp Tyr Gln Gln Lys Pro Gly Lys Ala Pro Lys Leu Leu Ile
         35                  40                  45 tac tac aca tca aca tta cac tca gga gtc cca tca agg ttc agt ggc    192
```

```
Tyr Tyr Thr Ser Thr Leu His Ser Gly Val Pro Ser Arg Phe Ser Gly
     50                  55                  60 agt ggg tct gga aca gat tat act ctc acc att agc agc ctg cag cca    240
Ser Gly Ser Gly Thr Asp Tyr Thr Leu Thr Ile Ser Ser Leu Gln Pro
65                  70                  75                  80 gaa gat ttt gcc act tac tat tgc caa cag ggt aat acg ctt cct tgg    288
Glu Asp Phe Ala Thr Tyr Tyr Cys Gln Gln Gly Asn Thr Leu Pro Trp
                85                  90                  95 acg ttc ggt gga ggt acc aat gtg gaa                                315
Thr Phe Gly Gly Gly Thr Asn Val Glu
            100                 105
```

<210> SEQ ID NO 31
<211> LENGTH: 105
<212> TYPE: PRT
<213> ORGANISM: Artificial Sequence
<220> FEATURE:
<223> OTHER INFORMATION: Wherein the amino acids represent the light
      chain encoding sequence of the humanized B9, AB9HZLC1-1

<400> SEQUENCE: 31

```
Asp Ile Gln Met Thr Gln Ser Pro Ser Ser Leu Ser Ala Ser Val Gly
 1               5                  10                  15

Asp Arg Val Thr Ile Thr Cys Arg Ser Ser Gln Asp Ile Ser Asn Phe
                20                  25                  30

Leu Asn Trp Tyr Gln Gln Lys Pro Gly Lys Ala Pro Lys Leu Leu Ile
            35                  40                  45

Tyr Tyr Thr Ser Thr Leu His Ser Gly Val Pro Ser Arg Phe Ser Gly
     50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asn Thr Leu Pro Trp
                85                  90                  95

Thr Phe Gly Gly Gly Thr Asn Val Glu
            100                 105
```

<210> SEQ ID NO 32
<211> LENGTH: 120
<212> TYPE: DNA
<213> ORGANISM: Artificial Sequence
<220> FEATURE:
<223> OTHER INFORMATION: Wherein the nucleotides represent a synthetic
      humanized heavy chain variable region designed
      using human heavy chain subgroup I consensus
      sequence frameworks

<400> SEQUENCE: 32
tttttaaccg gtgtccactc ccaagttcag cttgtacagt ctggagctga ggtgaagaag     60
cctggggcct cagtgaaggt atcctgcaag gcttctggct acacattcag tagctactgg    120

<210> SEQ ID NO 33
<211> LENGTH: 114
<212> TYPE: DNA
<213> ORGANISM: Artificial Sequence
<220> FEATURE:
<223> OTHER INFORMATION: Wherein the nucleotides represent a synthetic
      humanized heavy chain variable region designed
      using human heavy chain subgroup I consensus
      sequence frameworks

<400> SEQUENCE: 33
cttctcattg tagttagtat taccacttct aggtaaaatc tctccaatcc actcaaggcc     60

```
ttgtccaggg gcctgcttta cccactctat ccagtagcta ctgaatgtgt agcc         114
```

```
<210> SEQ ID NO 34
<211> LENGTH: 114
<212> TYPE: DNA
<213> ORGANISM: Artificial Sequence
<220> FEATURE:
<223> OTHER INFORMATION: Wherein the nucleotides represent a synthetic
      humanized heavy chain variable region designed
      using human heavy chain subgroup I consensus
      sequence frameworks

<400> SEQUENCE: 34
ggtaatacta actacaatga gaagttcaag ggcaaggcca cattcactgc agatacatcc   60
accagcacag cctacatgga actcagcagc ctgagatctg aggacactgc cgtc         114
```

```
<210> SEQ ID NO 35
<211> LENGTH: 123
<212> TYPE: DNA
<213> ORGANISM: Artificial Sequence
<220> FEATURE:
<223> OTHER INFORMATION: Wherein the nucleotides represent a synthetic
      humanized heavy chain variable region designed
      using human heavy chain subgroup I consensus
      sequence frameworks

<400> SEQUENCE: 35
tctgctgggg cccttggtac tagctgagga gacggtgact aaggttcctt gaccccagta   60
gtccatagag cccctgacgc cgcgacttga acagtaatag acggcagtgt cctcagatct  120
cag                                                                123
```

```
<210> SEQ ID NO 36
<211> LENGTH: 27
<212> TYPE: DNA
<213> ORGANISM: Artificial Sequence
<220> FEATURE:
<223> OTHER INFORMATION: Wherein the nucleotides represent primers used
      to PCR amplify the humanized heavy chain

<400> SEQUENCE: 36
ttaaccggtg tccactccca agttcag                                      27
```

```
<210> SEQ ID NO 37
<211> LENGTH: 27
<212> TYPE: DNA
<213> ORGANISM: Artificial Sequence
<220> FEATURE:
<223> OTHER INFORMATION: Wherein the nucleotides represent primers used
      to PCR amplify the humanized heavy chain

<400> SEQUENCE: 37
gctggggccc ttggtactag ctgagga                                      27
```

NUCLEIC ACIDS ENCODING ANTI-HUMAN αvβ3 AND αvβ5 ANTIBODIES

The application is a continuation of U.S. Ser. No. 09/694,951, filed 24 Oct. 2000 now abandoned, which is a divisional of U.S. Ser. No. 09/199,149 filed 24 Nov. 1998 now U.S. Pat. No. 6,160,099.

FIELD OF THE INVENTION

This invention relates to novel humanized monoclonal antibodies (mAbs) and to the genes encoding same. More specifically, this invention relates to human monoclonal antibodies specifically reactive with several heterodimeric integrins. Such antibodies are useful for the therapeutic and/or prophylactic treatment of a variety of angiogenic associated diseases (e.g., cancer metastasis, rheumatoid arthritis, atherosclerosis) among other disorders.

BACKGROUND OF THE INVENTION

Integrins are a superfamily of cell adhesion receptors, which are heterodimeric transmembrane glycoproteins expressed on a variety of cells, and which are made up of a variety of alpha and beta chains. Among those integrins are those which carry the RGD ligand, wherein one protein chain is referred to as $\alpha_v$. The integrins or cell surface adhesion receptors which share the $\alpha_v$ chain include the vitronectin receptor $\alpha_v\beta_3$, expressed on a number of cells, including endothelial, smooth muscle, osteoclast, and tumor cells; and also the $\alpha_v\beta_5$, $\alpha_v\beta_6$, $\alpha_v\beta_8$ and $\alpha_v\beta_1$ receptors. These receptors are expressed primarily on cancer cells, such as tumor cells and in metastatic lesions. They are present on some immunohistologic lesions, in the placenta and are also involved angiogenic disorders involving the vasculature.

As one example, the $\alpha_v\beta_3$ receptor expressed on the membrane of osteoclast cells has been postulated to mediate the bone resorption process and contribute to the development of osteoporosis [Ross, et al., *J. Biol. Chem.*, 1993, 268 (13): 9901–7]. As another example, the $\alpha_v\beta_3$ receptor expressed on human aortic smooth muscle cells has been postulated to stimulate their migration into neointima, which leads to the formation of atherosclerosis and restenosis after angioplasty [Brown, et al., *Cardiovascular Res.*, 1994, 28: 1815]. The connection between antagonism of the vitronectin receptor and restenosis after vascular procedures was referred to by Choi et al, *J. Vasc. Surg.*, 1994, 19:125–34. International Patent Publication No. WO95/25543, published Mar. 9, 1995, refers to a method of inhibiting angiogenesis by administering an antagonist of the vitronectin receptor.

Additionally, a recent study referred to an $\alpha_v\beta_3$ antagonist as promoting tumor regression by inducing apoptosis of angiogenic blood vessels [P. C. Brooks, et al., *Cell*, 1994, 79: 1157–1164]. Similarly a murine monoclonal antibody LM609 developed to the vitronectin receptor reported in International Patent Publication No. WO89/05155, published Jun. 15, 1995, was referred to as useful in the inhibition of tumor growth. See, also, D. A. Cheresh et al, *Cell*, 1989, 57:59–69.

While passive immunotherapy employing monoclonal antibodies from a heterologous species (e.g., murine) has been suggested as a useful mechanism for treating or preventing various diseases or disorders, one alternative to reduce the risk of an undesirable immune response on the part of the patient directed against the foreign antibody is to employ "humanized" antibodies. These antibodies are substantially of human origin, with only the Complementarity Determining Regions (CDRs) and certain framework residues that influence CDR conformation being of non-human origin. Particularly useful examples of this approach for the treatment of some disorders are disclosed in PCT Application PCT/GB91/01554, Publication No. WO 92/04381 and PCT Application PCT/GB93/00725, Publication No. WO93/20210.

Novel human mABs or humanized antibodies are particularly useful alone or in combination with existing molecules to form immunotherapeutic compositions. There remains a need in the art for additional mAbs to cell surface receptors or humanized antibodies thereto which can selectively block the integrin and display a long serum half-life.

SUMMARY OF THE INVENTION

In one aspect, this invention relates to a novel humanized monoclonal antibody which neutralizes the biological function of receptors which carry the $\alpha_v$ chain. Specifically, this antibody is reactive with a variety of such heterodimeric integrins and functional fragments thereof which carry the $\alpha_v$ subunit chain. This humanized antibody specifically neutralizes the human $\alpha_v\beta_3$ (vitronectin receptor) and the human $\alpha_v\beta_5$ receptor.

In a related aspect, the present invention provides modifications to neutralizing Fab fragments or F(ab')$_2$ fragments specific for the human $\alpha_v\beta_3$ and $\alpha_v\beta_5$ receptors produced by random combinatorial cloning of human antibody sequences and isolated from a filamentous phage Fab display library.

In still another aspect, there is provided a reshaped human antibody containing human heavy and light chain constant regions from a first human donor and heavy and light chain variable regions or the CDRs thereof derived from human neutralizing monoclonal antibodies for the human $\alpha_v\beta_3$/$\alpha_v\beta_5$ receptors derived from a second human donor.

In yet another aspect, the present invention provides a pharmaceutical composition which contains one (or more) altered antibodies and a pharmaceutically acceptable carrier.

In a further aspect, the present invention provides a method for passive immunotherapy of a disorder mediated by a receptor carrying the $\alpha_v$ subunit, such as all cancers characterized by solid tumors that metastasize, lymphomas that express these receptors; angiogenesis of the target of the tumors, restenosis, rheumatoid arthritis or atherosclerosis, among others, in a human by administering to said human an effective amount of the pharmaceutical composition of the invention for the prophylactic or therapeutic treatment of the disorder.

In still another aspect, the invention provides a method for treating a disease which is mediated by an $\alpha_v$-containing heterodimeric integrin in a human, by administering to the human an immunotherapeutically effective amount of the antibody of the invention, followed by administering to said human a therapeutically effective amount of a small chemical molecule which is an antagonist of the integrin receptor. These antibodies may also be co-administered with other drugs which are known for the treatment of the particular cancer or angiogenic disorder.

In yet another aspect, the present invention provides methods for, and components useful in, the recombinant production of humanized and altered antibodies (e.g., engineered antibodies, CDRs, Fab or F(ab)$_2$ fragments, or analogs thereof) which are derived from neutralizing monoclonal antibodies (mAbs) for the human $\alpha_v$-containing receptors. These components include isolated nucleic acid sequences encoding same, as well as recombinant plasmids containing the nucleic acid sequences under the control of selected regulatory sequences which are capable of directing the expression thereof in host cells (preferably mammalian) transfected with the recombinant plasmids. The production method involves culturing a transfected host cell of the present invention under conditions such that the human or altered antibody is expressed in said cell and isolating the expressed product therefrom.

Yet another aspect of the invention is a method to diagnose the overexpression of the human $\alpha_v$-containing receptor in a human. The method includes contacting a biopsy sample with the antibodies and altered antibodies of the instant invention and assaying for the occurrence of binding between said antibody (or altered antibody) and the human $\alpha_v$-containing heterodimeric receptor using a conventional imaging system.

Yet another embodiment of the invention is a pharmaceutical composition comprising at least one dose of an immunotherapeutically effective amount of the antibodies of this invention in combination with at least one additional monoclonal or altered antibody. A particularly desirable composition comprises as the additional antibody, an anti-human $\alpha_v\beta_3$ receptor antibody, which is distinguished from the subject antibody by virtue of being reactive with a different epitope of the heterodimeric human $\alpha_v\beta_3$ receptor. One such example is the D12 antibody described in International Patent Application No. WO98/40488, published Sep. 17, 1998.

Other aspects and advantages of the present invention are described further in the detailed description and the preferred embodiments thereof.

BRIEF DESCRIPTION OF THE DRAWINGS

FIG. 1A illustrates the heavy chain variable region DNA and amino acid sequences of the murine mAb B9 [SEQ ID NOS: 1, 2 and 38], in which the CDRs are represented in bold and underlined.

FIG. 1B is the heavy chain variable region amino acid sequence of the human VH subgroup I consensus amino acid sequence [SEQ ID NO: 3], in which the CDRs are represented in bold and underlined.

FIG. 1C illustrates the synthetic heavy chain variable region DNA and amino acid sequences of the consensus, humanized heavy chain B9 HZHC 1-0[SEQ ID NOS: 4 and 5], in which the CDRs are represented in bold and underlined. Asterisks above the amino acids indicate preferred murine framework residues retained in the synthetic heavy chain.

FIG. 2A illustrates the light chain DNA and amino acid sequences of the murine mAb B9 [SEQ ID NOS: 6, 7 and 39], in which the CDRs are represented in bold and underlined.

FIG. 2B is the light chain amino acid sequence of the human V kappa subgroup I consensus amino acid sequence of [SEQ ID NO: 8], in which the CDRs are represented in bold and underlined.

FIG. 2C is the synthetic light chain amino acid DNA and amino acid sequence of the consensus, synthetic, humanized light chain B9 HZLC1-0 [SEQ ID NOS: 9, 10 and 40], in which the CDRs are represented in bold and underlined. Asterisks indicate preferred murine framework residues and are illustrated above the amino acid residue.

FIG. 3 illustrates the DNA and amino acid sequences representing the intermediate of the synthetic B9 heavy chain variable region [SEQ ID NOS: 11, 12 and 41]. The endonuclease enzyme restriction sites are underlined.

FIG. 4 illustrates the DNA and amino acid sequences representing the intermediate of the synthetic B9 light chain variable region [SEQ ID NOS: 13, 14 and 42]. The endonuclease enzyme restriction sites are underlined.

FIG. 5 is the amino acid sequence of the modified human REI kappa V region framework with the CDRs underlined and in bold type. The last QQ of the sequence represents the first two amino acids of the third CDR [SEQ ID NO: 15].

FIG. 6 illustrates the DNA and amino acid sequences [SEQ ID NOS: 28, 29 and 43] representing a light chain encoding sequence of humanized B9 AB9 HZLCREI≅. The CDRs are shown in bold print.

FIG. 7 illustrates the DNA and amino acid sequences [SEQ ID NOS: 30, 31 and 44] of the light chain encoding sequence of the humanized B9, AB9 HZLCl-1≅.

DETAILED DESCRIPTION OF THE INVENTION

Figure 8:
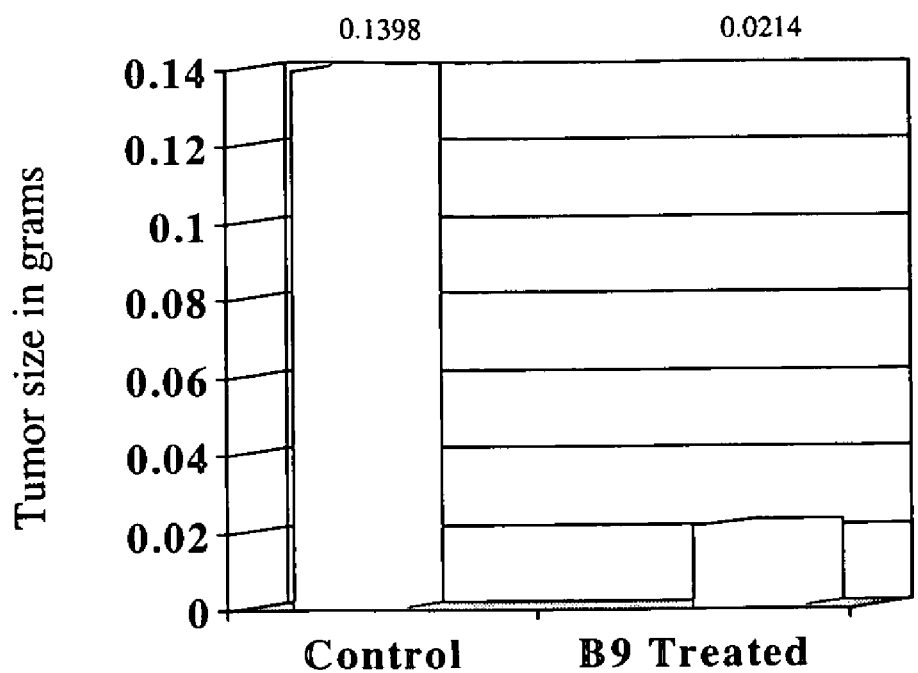
FIG. 8 is a graph showing the results of the mouse tumor xenograft model with HT29 assay of Example 14, with the cells injected i.p.

The present invention provides useful antibodies, including monoclonal, recombinant and synthetic antibodies (and fragments thereof) which neutralize the human vitronectin $\alpha_v\beta_3$ receptor and the human $\alpha_v\beta_5$ receptors, as well as bind to other integrins bearing the $\alpha_v$ subunit; isolated nucleic acids encoding same and various means for their recombinant production as well as therapeutic, prophylactic and diagnostic uses of such antibodies and fragments thereof.

The antibodies of this invention inhibit the binding of vitronectin and other ligands to the vitronectin ($\alpha_v\beta_3$) receptor. The antibodies of this invention inhibit the binding of ligands to the $\alpha_v\beta_5$ receptor. These antibodies may also inhibit the binding of ligands to the $\alpha_v\beta_1$ and $\alpha_v\beta_6$ and $\alpha_v\beta_8$ receptors. These antibodies can selectively block the integrins $\alpha_v\beta_3$ and $\alpha_v\beta_5$ and display a serum half-life of approximately 60 hours in vivo in animal models. Specifically, the antibodies including the murine monoclonal B9 and the humanized antibody HuB9, which specifically neutralize $\alpha_v\beta_3$ and $\alpha_v\beta_5$, are desirable for use as acute and subacute therapeutic reagents for the treatment of the disorders mediated by these receptors. Inhibition of these receptors by the antibodies of this invention permits therapeutic treatment or prophylaxis of such diseases.

I. Definitions.

As used in this specification and the claims, the following terms are defined as follows:

The phrase "disorders mediated by $\alpha_v$-containing heterodimeric receptors" includes, but is not limited to, cardiovascular disorders or angiogenic-related disorders, such as cancers, e.g., solid tumor and metastases, angiogenesis associated with diabetic retinopathy, atherosclerosis and restenosis, chronic inflammatory disorders, macular degeneration, and diseases wherein bone resorption is associated with pathology such as osteoporosis. The antibodies of this invention are primarily useful also as anti-metastatic and antitumor agents.

"Altered antibody" refers to a protein encoded by an immunoglobulin coding region altered from its natural form, which may be obtained by expression in a selected host cell.

Such altered antibodies are engineered antibodies (e.g., chimeric, humanized, or reshaped or immunologically edited human antibodies) or fragments thereof lacking all or part of an immunoglobulin constant region, e.g., Fv, Fab, or F(ab')$_2$ and the like.

"Altered immunoglobulin coding region" refers to a nucleic acid sequence encoding an altered antibody of the invention or a fragment thereof.

"Reshaped human antibody" refers to an altered antibody in which minimally at least one CDR from a first human monoclonal donor antibody is substituted for a CDR in a second human acceptor antibody. Preferably all six CDRs are replaced. More preferably an entire antigen combining region, for example, an Fv, Fab or F(ab')$_2$, from a first human donor monoclonal antibody is substituted for the corresponding region in a second human acceptor monoclonal antibody. Most preferably the Fab region from a first human donor is operatively linked to the appropriate constant regions of a second human acceptor antibody to form a full length monoclonal antibody.

"First immunoglobulin partner" refers to a nucleic acid sequence encoding a human framework or human immunoglobulin variable region in which the native (or naturally-occurring) CDR-encoding regions are replaced by the CDR-encoding regions of a donor human antibody. The human variable region can be an immunoglobulin heavy chain, a light chain (or both chains), an analog or functional fragment thereof. Such CDR-encoding regions, located within the variable region of antibodies (immunoglobulins) can be determined by known methods in the art. For example Kabat et al, *Sequences of Proteins of Immunological Interest*, 4th Ed., U.S. Department of Health and Human Services, National Institutes of Health (1987) disclose rules for locating CDRs. In addition, computer programs are known which are useful for identifying CDR regions/structures.

"Second fusion partner" refers to another nucleotide sequence encoding a protein or peptide to which the first immunoglobulin partner is fused in frame or by means of an optional conventional linker sequence (i.e., operatively linked). Preferably the fusion partner is an immunoglobulin gene and when so, it is referred to as a "second immunoglobulin partner". The second immunoglobulin partner may include a nucleic acid sequence encoding the entire constant region for the same (i.e., homologous—the first and second altered antibodies are derived from the same source) or an additional (i.e., heterologous) antibody of interest. It may be an immunoglobulin heavy chain or light chain, or both chains as part of a single polypeptide. The second immunoglobulin partner is not limited to a particular immunoglobulin class or isotype. In addition, the second immunoglobulin partner may comprise part of an immunoglobulin constant region, such as found in a Fab, or F(ab)$_2$ (i.e., a discrete part of an appropriate human constant region or framework region). A second fusion partner may also comprise a sequence encoding an integral membrane protein exposed on the outer surface of a host cell, e.g., as part of a phage display library, or a sequence encoding a protein for analytical or diagnostic detection, e.g., horseradish peroxidase, β-galactosidase, etc.

The terms Fv, Fc, Fd, Fab, or F(ab')$_2$ are used with their standard meanings [see, e.g., Harlow et al, *Antibodies A Laboratory Manual*, Cold Spring Harbor Laboratory, (1988)].

As used herein, an "engineered antibody" describes a type of altered antibody, i.e., a full-length synthetic antibody (e.g., a chimeric, humanized, reshaped or immunologically edited human antibody as opposed to an antibody fragment) in which a portion of the light and/or heavy chain variable domains of a selected acceptor antibody are replaced by analogous parts from one or more donor antibodies which have specificity for the selected epitope. For example, such molecules may include antibodies characterized by a humanized heavy chain associated with an unmodified light chain (or chimeric light chain), or vice versa. Engineered antibodies may also be characterized by alteration of the nucleic acid sequences encoding the acceptor antibody light and/or heavy variable domain framework regions in order to retain donor antibody binding specificity. These antibodies can comprise replacement of one or more CDRs (preferably all) from the acceptor antibody with CDRs from a donor antibody described herein.

A "chimeric antibody" refers to a type of engineered antibody which contains a naturally-occurring variable region (light chain and heavy chain) derived from a donor antibody in association with light and heavy chain constant regions derived from an acceptor antibody from a heterologous species.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity [see, e.g., Queen et al., 1991, *Proc. Nat'l. Acad. Sci. USA*, 86:10029–10032 and Hodgson et al., 1991, *Biotechnology*, 9:421].

An "immunologically edited antibody" refers to a type of engineered antibody in which changes are made in donor and/or acceptor sequences to edit regions involving cloning artifacts, germ line enhancements, etc. aimed at reducing the likelihood of an immunological response to the antibody on the part of a patient being treated with the edited antibody.

The term "donor antibody" refers to an antibody (monoclonal, or recombinant) which contributes the nucleic acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody. One donor antibody suitable for use in this invention is a neutralizing murine monoclonal anti-$\alpha_v\beta_3$ and anti-$\alpha_v\beta_5$ antibody, designated as B9. B9 is defined as having the variable heavy chain and variable light chain amino acid sequences shown in FIGS. 1A and 2A, respectively [SEQ ID NOS: 2 and 7].

The term "acceptor antibody" refers to an antibody (monoclonal, or recombinant) from a source genetically unrelated to the donor antibody, which contributes all (or any portion, but preferably all) of the nucleic acid sequences encoding its heavy and/or light chain framework regions and/or its heavy and/or light chain constant regions to the first immunoglobulin partner. Preferably a human antibody is the acceptor antibody.

"Consensus VH" or "Consensus VL" regions refers to amino acid sequences which can function in a manner similar to the framework regions of the acceptor antibody, but are selected by conventional computer techniques. Briefly, provided with a given VH or VL amino acid sequence, the human VH and VL sequences closest to the given sequence are assembled to identify the closest antibody subgroup. Once the subgroup is selected, all human antibodies from that subgroup are compared and a consensus sequence of the VH and VL chains are prepared. The consensus sequences are used to generate a desirable synthetic framework region for the humanized antibody.

"CDRs" are the complementarity determining region amino acid sequences of an antibody. CDRs are the hypervariable regions of immunoglobulin heavy and light chains. See, e.g., Kabat et al, *Sequences of Proteins of Immunological Interest*, 4th Ed., U.S. Department of Health and Human Services, National Institutes of Health (1987). There are three heavy chain CDRs and three light chain CDRs (or CDR regions) in the variable portions of an immunoglobulin. Thus, "CDRs" as used herein refers to all three heavy chain CDRs, or all three light chain CDRs (or both all heavy and all light chain CDRs, if appropriate). CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

By "sharing the antigen binding specificity or neutralizing ability" is meant, for example, that although mAb B9 may be characterized by a certain level of antigen affinity, a CDR encoded by a nucleic acid sequence of mAb B9 in an appropriate structural environment may have a lower, or higher affinity. It is expected that CDRs of mAb B9 in such environments will nevertheless recognize the same epitope (s) as does the intact mAb B9.

A "functional fragment" is a partial heavy or light chain variable sequence (e.g., minor deletions at the amino or carboxy terminus of the immunoglobulin variable region) which retains the same antigen binding specificity and/or neutralizing ability as the antibody from which the fragment was derived.

An "analog" is an amino acid sequence modified by at least one amino acid, wherein said modification can be a chemical modification or substitution onto an amino acid or a substitution or a rearrangement of a few amino acids (i.e., no more than 10), which modification permits the amino acid sequence to retain the biological characteristics, e.g., antigen specificity and high affinity, of the unmodified sequence. For example, different humanized variants can be constructed using the sequences disclosed herein.

Analogs may also arise as allelic variations. An "allelic variation or modification" is an alteration in the nucleic acid sequence encoding the amino acid or peptide sequences of the invention. Such variations or modifications may be due to degeneracy in the genetic code or may be deliberately engineered to provide desired characteristics. These variations or modifications may or may not result in alterations in any encoded amino acid sequence. For example, silent mutations can be constructed, via substitutions, when certain endonuclease restriction sites are created within or surrounding CDR-encoding regions.

The term "effector agents" refers to non-protein carrier molecules to which the altered antibodies, and/or natural or synthetic light or heavy chains of the donor antibody or other fragments of the donor antibody may be associated by conventional means. Such non-protein carriers can include conventional carriers used in the diagnostic field, e.g., polystyrene or other plastic beads, polysaccharides, e.g., as used in the BIAcore® (Pharmacia) system, or other non-protein substances useful in the medical field and safe for administration to humans and animals. Other effector agents may include a macrocycle, for chelating a heavy metal atom, or radioisotopes. Such effector agents may also be useful to increase the half-life of the altered antibodies, e.g., polyethylene glycol.

II. Murine Monoclonal Antibodies that Bind $\alpha_v$-containing Heterodimers

For use in constructing the humanized antibodies, fragments and fusion proteins of this invention, a non-human species may be employed to generate a desirable immunoglobulin upon presentment with a human $\alpha_v$-containing heterodimeric receptor as antigen. Conventional hybridoma techniques are employed to provide a hybridoma cell line secreting a non-human monoclonal antibody (mAb) to the $\alpha_v$-containing receptors. As one example, the production of murine mAb B9 is described in detail in Example 2 below. For ease of discussion below, the term B9 may refer to the B9 mAb or any of the other mAbs of Example 2.

B9 is a desirable donor antibody for use in developing a chimeric or humanized antibody of this invention. The characteristics of the neutralizing murine mAb B9 obtained as described in Example 2 include an antigen binding specificity for human $\alpha_v\beta_3$ and $\alpha_v\beta_5$, and possibly other $\alpha_v$-containing heterodimeric receptors, and characteristics listed in Table I below. The isotype of the mAb B9 of Example 2 is $IgG_1$, and it has an affinity of between about 0.1 and 0.3 nM against $\alpha_v\beta_3$ and $\alpha_v\beta_5$ receptors, depending on the assay employed. The antibody recognizes the $\alpha_v$ subunit of the heterodimeric $\alpha_v\beta_3$ and $\alpha_v\beta_5$ receptors and does not recognize either β subunit individually. The binding is illustrated by binding and functional activity (neutralization) in the in vitro assays of Examples 3–10 below.

Given the sequences provided, i.e. the light chain variable region of B9 [SEQ ID NO: 6] and the heavy chain variable region of B9 [SEQ ID NO: 1], one of skill in the art could obtain the remaining portions of the heavy chain using, for example, polymerase chain reaction, and thus obtain a complete mAb molecule. Alternatively, a B9 molecule could be constructed using techniques analogous to those described below for the synthetic and recombinant mAbs of the invention and employing other murine IgG subtype heavy chains.

Other anti-$\alpha_v$ subunit antibodies may be developed by screening hybridomas or combinatorial libraries, or antibody phage displays [W. D. Huse et al., 1988, *Science*, 246: 1275–1281] using the murine mAb described herein and its $\alpha_v$ epitope. A collection of antibodies, including hybridoma products or antibodies derived from any species immunoglobulin repertoire may be screened in a conventional competition assay, such as described in Examples 5, 8 and 9 below, with one or more epitopes described herein. Thus, the invention may provide an antibody, other than B9, which is capable of binding to and neutralizing the $\alpha_v$-containing receptors. Other mAbs generated against a desired $\alpha_v$ or suitable β chain epitope and produced by conventional techniques, include without limitation, genes encoding murine mAbs, human mAbs, and combinatorial antibodies.

This invention is not limited to the use of the B9 mAb or its hypervariable sequences. It is anticipated that any appropriate $\alpha_v\beta_3$ or $\alpha_v\beta_5$ neutralizing antibodies and corresponding anti-$\alpha_v$ CDRs described in the art may be substituted therefor. Wherever in the following description the donor antibody is identified as B9, this designation is made for illustration and simplicity of description only.

III. Combinatorial Cloning to Obtain Human Antibodies

As mentioned above, a number of problems have hampered the direct application of the hybridoma technology of G. Kohler and C. Milstein, 1975, *Nature*, 256: 495–497 to the generation and isolation of human monoclonal antibodies. Among these are a lack of suitable fusion partner myeloma cell lines used to form hybridoma cell lines as well as the poor stability of such hybridomas even when formed. Therefore, the molecular biological approach of combinatorial cloning is preferred.

Combinatorial cloning is disclosed generally in PCT Publication No. WO90/14430. Simply stated, the goal of combinatorial cloning is to transfer to a population of bacterial cells the immunological genetic capacity of a human cell, tissue or organ. It is preferred to employ cells, tissues or organs which are immunocompetent. Particularly useful sources include, without limitation, spleen, thymus, lymph nodes, bone marrow, tonsil and peripheral blood lymphocytes. The cells may be optionally stimulated with the human $\alpha_v\beta_3$ receptor in vitro, or selected from donors which are known to have produced an immune response or donors who are HIV$^+$ but asymptomatic.

The genetic information (i.e., the human antibodies produced in the tissues in response to stimulation by $\alpha_v$-containing heterodimeric integrin antigen) isolated from the donor cells can be in the form of DNA or RNA and is conveniently amplified by PCR or similar techniques. When isolated as RNA, the genetic information is preferably converted into cDNA by reverse transcription prior to amplification. The amplification can be generalized or more specifically tailored. For example, by a careful selection of PCR primer sequences, selective amplification of immunoglobulin genes or subsets within that class of genes can be achieved.

Once the component gene sequences are obtained, in this case the genes encoding the variable regions of the various heavy and light antibody chains, the light and heavy chain genes are associated in random combinations to form a random combinatorial library. Various recombinant DNA vector systems have been described to facilitate combinatorial cloning [see, e.g., PCT Publication No. WO90/14430 supra, Scott and Smith, 1990, *Science*, 249:386–406 or U.S. Pat. No. 5,223,409]. Having generated the combinatorial library, the products can, after expression, be conveniently screened by biopanning with the selected human $\alpha_v$-containing receptor or, if necessary, by epitope blocked biopanning as described in more detail below.

Initially it is generally preferred to use Fab fragments of mAbs, such as B9, for combinatorial cloning and screening and then to convert the Fabs to full length mAbs after selection of the desired candidate molecules. However, single chain antibodies can also be used for cloning and screening.

IV. Antibody Fragments

The present invention contemplates the use of Fab fragments or F(ab')$_2$ fragments to derived full-length mAbs directed against the human integrin $\alpha_v\beta_3$ or $\alpha_v\beta_5$ receptor. Although these fragments may be independently useful as protective and therapeutic agents in vivo against conditions mediated by the human $\alpha_v$-containing receptors or in vitro as part of a diagnostic for a disease mediated by the human $\alpha_v$-containing receptor, they are employed herein as a component of a reshaped human antibody. A Fab fragment contains the entire light chain and amino terminal portion of the heavy chain; and a F(ab')$_2$ fragment is the fragment formed by two Fab fragments bound by additional disulfide bonds. Human $\alpha_v$-containing receptor binding monoclonal antibodies of the present invention provide sources of Fab fragments and F(ab')$_2$ fragments, which latter fragments can be obtained from combinatorial phage library [see, e.g., Winter et al., 1994, *Ann. Rev. Immunol.*, 12:433–455 or Barbas et al., 1992, *Proc. Nat'l. Acad. Sci. USA*, 89:10164–10168 which are both hereby incorporated by reference in their entireties]. These Fab and F(ab')$_2$ fragments are useful themselves as therapeutic, prophylactic or diagnostic agents, and as donors of sequences including the variable regions and CDR sequences useful in the formation of recombinant or humanized antibodies as described herein.

V. Anti-human Antibody Amino Acid and Nucleotide Sequences of Interest

The mAb B9 or other antibodies described herein may contribute sequences, such as variable heavy and/or light chain peptide sequences, framework sequences, CDR sequences, functional fragments, and analogs thereof, and the nucleic acid sequences encoding them, useful in designing and obtaining various altered antibodies which are characterized by the antigen binding specificity of the donor antibody.

As one example, the present invention thus provides variable light chain and variable heavy chain sequences from the anti-human mAb B9 and sequences derived therefrom. The DNA and amino acid sequences of the heavy chain variable region of mAb B9 are reported illustrated by FIG. 1A [SEQ ID NOS: 1, 2 and 38]. The nucleotide and amino acid sequences of the light chain variable region of mAb B9 are reported in FIG. 2A [SEQ ID NOS: 6, 7 and 39].

The nucleic acid sequences of this invention, or fragments thereof, encoding the variable light chain and heavy chain peptide sequences are also useful for mutagenic introduction of specific changes within the nucleic acid sequences encoding the CDRs or framework regions, and for incorporation of the resulting modified or fusion nucleic acid sequence into a plasmid for expression. For example, silent substitutions in the nucleotide sequence of the framework and CDR-encoding regions can be used to create restriction enzyme sites which would facilitate insertion of mutagenized CDR (and/or framework) regions. These CDR-encoding regions may be used in the construction of reshaped human antibodies of this invention.

Taking into account the degeneracy of the genetic code, various coding sequences may be constructed which encode the variable heavy and light chain amino acid sequences, and CDR sequences of the invention as well as functional fragments and analogs thereof which share the antigen specificity of the donor antibody. The isolated nucleic acid sequences of this invention, or fragments thereof, encoding the variable chain peptide sequences or CDRs can be used to produce altered antibodies, e.g., chimeric or humanized antibodies, or other engineered antibodies of this invention when operatively combined with a second immunoglobulin partner.

It should be noted that in addition to isolated nucleic acid sequences encoding portions of the altered antibody and antibodies described herein, other such nucleic acid sequences are encompassed by the present invention, such as those complementary to the native CDR-encoding sequences or complementary to the modified human framework regions surrounding the CDR-encoding regions. Such sequences include all nucleic acid sequences which by virtue of the redundancy of the genetic code are capable of encoding the same amino acid sequences as provided in FIGS. 1A and 2A. An exemplary humanized light chain variable sequence is illustrated in FIG. 2C [SEQ ID NO: 9]. An exemplary humanized heavy chain variable sequence is illustrated in FIG. 1C [SEQ ID NO: 4]. These heavy chain and the light chain variable regions have three CDR sequences described in detail in the murine sequences of FIGS. 1A and 2A.

Other useful DNA sequences encompassed by this invention include those sequences which hybridize under stringent hybridization conditions [see, e.g., T. Maniatis et al., 1982, *Molecular Cloning (A Laboratory Manual)*, Cold Spring Harbor Laboratory pages 387 to 389] to the DNA sequences encoding the light and heavy chain variable regions of FIGS. 1A and 2A (also including FIGS. 1C and 2C for the synthetic human sequences) and which retain the antigen binding properties of those antibodies. An example of one such stringent hybridization condition is hybridization at 4× SSC at 65° C., followed by a washing in 0.1× SSC at 65° C. for an hour. Alternatively an exemplary stringent hybridization condition is in 50% formamide, 4× SSC at 42° C. Preferably, these hybridizing DNA sequences are at least about 18 nucleotides in length, i.e., about the size of a CDR. Other useful DNA sequences are those which are over 60%, preferably over 70% and more preferably over 80% or 90% homologous to the sequence or fragments of sequence of mAb B9.

Where in this specification, protein and/or DNA sequences are defined by their percent homologies or identities to identified sequences, the algorithms used to calculate the percent identities or percent similarities include the following: the Smith-Waterman algorithm [J. F. Collins et al, 1988, *Comput. Appl. Biosci.*, 4:67–72; J. F. Collins et al, Molecular Sequence Comparison and Alignment, (M. J. Bishop et al, eds.) In Practical Approach Series: Nucleic Acid and Protein Sequence Analysis XVIII, IRL Press: Oxford, England, UK (1987) pp. 417], e.g., MPSEARCH, and the BLAST and FASTA programs [E. G. Shpaer et al, 1996, *Genomics*, 38:179–191], including the BLAST2 program [S. D. Altschul et al, *J. Mol. Biol.*, 215:403–407 (1990)]. These references are incorporated herein by reference.

VI. Altered Immunoglobulin Coding Regions and Altered Antibodies

Altered immunoglobulin coding regions encode altered antibodies which include engineered antibodies such as chimeric antibodies, humanized, reshaped and immunologically edited human antibodies. A desired altered immunoglobulin coding region contains CDR-encoding regions in the form of Fab regions that encode peptides having the antigen specificity of the anti-human B9 antibody, preferably a high affinity antibody such as provided by the present invention, inserted into an acceptor immunoglobulin partner.

When the acceptor is an immunoglobulin partner, as defined above, it includes a sequence encoding a second antibody region of interest, for example an Fc region. Immunoglobulin partners may also include sequences encoding another immunoglobulin to which the light or heavy chain constant region is fused in frame or by means of a linker sequence. Engineered antibodies directed against functional fragments or analogs of the selected human $\alpha_v$-subunit-containing integrin may be designed to elicit enhanced binding with the same antibody.

The immunoglobulin partner may also be associated with effector agents as defined above, including non-protein carrier molecules, to which the immunoglobulin partner may be operatively linked by conventional means.

Fusion or linkage between the immunoglobulin partners, e.g., antibody sequences, and the effector agent may be by any suitable means, e.g., by conventional covalent or ionic bonds, protein fusions, or hetero-bifunctional cross-linkers, e.g., carbodiimide, glutaraldehyde, and the like. Such techniques are known in the art and readily described in conventional chemistry and biochemistry texts.

Additionally, conventional linker sequences which simply provide for a desired amount of space between the second immunoglobulin partner and the effector agent may also be constructed into the altered immunoglobulin coding region. The design of such linkers is well known to those of skill in the art.

In addition, signal sequences for the molecules of the invention may be modified to enhance expression. For example, the reshaped human antibody having the signal sequence and CDRs derived from the mAb B9 heavy chain sequence, may have the original signal peptide replaced with another signal sequence, such as the Campath leader sequence [Page, M. J. et al., 1991, *BioTechnology*, 9:64–68].

An exemplary altered antibody, a reshaped human antibody, contains a variable heavy and the entire light chain peptide or protein sequence having the antigen specificity of mAb B9 fused to the constant heavy regions $C_{H1}$ $C_{H3}$ derived from a second human antibody.

In still a further embodiment, the engineered antibody of the invention may have attached to it an additional agent. For example, the procedure of recombinant DNA technology may be used to produce an engineered antibody of the invention in which the Fc fragment or $C_{H2}$ $C_{H3}$ domain of a complete antibody molecule has been replaced by an enzyme or other detectable molecule (i.e., a polypeptide effector or reporter molecule).

Another desirable protein of this invention may comprise a complete antibody molecule, having full length heavy and light chains, or any discrete fragment thereof, such as the Fab or F(ab')$_2$ fragments, a heavy chain dimer, or any minimal recombinant fragments thereof such as an F$_v$ or a single-chain antibody (SCA) or any other molecule with the same specificity as the selected donor mAb B9. Such protein may be used in the form of an altered antibody, or may be used in its unfused form.

Whenever the immunoglobulin partner is derived from an antibody different from the donor antibody, e.g., any isotype or class of immunoglobulin framework or constant regions, or is selected by a computer program as a consensus sequence, as defined above, an engineered antibody results. Engineered antibodies can comprise immunoglobulin (Ig) constant regions and variable framework regions from one source, e.g., the acceptor antibody or consensus sequences, and one or more (preferably all) CDRs from the donor antibody, e.g., the anti-human B9 antibody described herein. In addition, alterations, e.g., deletions, substitutions, or additions, of the acceptor mAb light and/or heavy variable domain framework region at the nucleic acid or amino acid levels, or the donor CDR regions may be made in order to retain donor antibody antigen binding specificity or to reduce potential immunogenicity.

Such engineered antibodies are designed to employ one (or both) of the variable heavy and/or light chains of the anti-human $\alpha_v$ subunit-containing receptor mAb (optionally modified as described) or one or more of the below-identified heavy or light chain CDRs. The engineered antibodies of the invention are neutralizing, i.e., they desirably inhibit ligand binding to the $\alpha_v\beta_3$ or $\alpha_v\beta_5$ receptor in vitro and in vivo in animal models of diseases mediated by these receptors, e.g., cancers.

Such engineered antibodies may include a reshaped human antibody containing the human heavy and light chain constant regions fused to the human anti-$\alpha_v\beta_3/\alpha_v\beta_5$ antibody functional fragments. A suitable human (or other animal)

acceptor antibody may be one selected from a conventional database, e.g., the KABAT[7] database, Los Alamos database, and Swiss Protein database, by homology to the nucleotide and amino acid sequences of the donor antibody. Alternatively, a consensus sequence formed by all known human sequences in the database of a subgroup closest to that of the donor antibody may be used to supply the framework regions. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody.

Desirably the heterologous framework and constant regions are selected from human immunoglobulin classes and isotypes, such as IgG (subtypes 1 through 4), IgM, IgA and IgE. The Fc domains are not limited to native sequences, but include mutant variants known in the art that alter function. For example, mutations have been described in the Fc domains of certain IgG antibodies that reduce Fc-mediated complement and Fc receptor binding [see, e.g., A. R. Duncan et al., 1988, *Nature*, 332:563–564; A. R. Duncan and G. Winter, 1988, *Nature*, 332:738–740; M.-L. Alegre et al., 1992, *J. Immunol.*, 148:3461–3468; M.-H. Tao et al., 1993, *J. Exp. Med.*, 178:661–667; V. Xu et al, 1994, *J. Biol. Chem.*, 269:3469–2374] and alter clearance rate [J.-K. Kim et al., 1994, *Eur. J. Immunol.*, 24:542–548] and reduce structural heterogeneity [S. Angal et al., 1993, *Mol. Immunol.*, 30:105–108]. Also, other modifications are possible such as oligomerization of the antibody by addition of the tailpiece segment of IgM and other mutations [R. I. F. Smith and S. L. Morrison, 1994, *Biotechnology*, 12:683–688; R. I. F. Smith et al., 1995, *J. Immunol.*, 154: 2226–2236] or addition of the tailpiece segment of IgA [I. Kariv et al., 1996, *J. Immunol.*, 157: 29–38]. However, the acceptor antibody need not comprise only human immunoglobulin protein sequences. For instance, a gene may be constructed in which a DNA sequence encoding part of a human immunoglobulin chain is fused to a DNA sequence encoding a non-immunoglobulin amino acid sequence such as a polypeptide effector or reporter molecule.

One example of a particularly desirable altered antibody is a humanized antibody containing all or a portion of the variable domain amino acid sequences of B9 and some portions of the donor antibody framework regions, or CDRs therefrom inserted onto the framework regions of a selected human antibody. This humanized antibody is directed against human $\alpha_v\beta_3$ and $\alpha_v\beta_5$ receptors, among others. Suitably, in these humanized antibodies one, two or preferably three CDRs from the B9 antibody heavy chain and/or light chain variable regions are inserted into the framework regions of a selected human antibody or consensus sequence, replacing the native CDRs of that latter antibody or consensus sequence.

Preferably, in a humanized antibody, the variable domains in both human heavy and light chains have been engineered by one or more CDR replacements. It is possible to use all six CDRs, or various combinations of less than the six CDRs. For example, it is possible to replace the CDRs only in the human heavy chain, using as light chain the unmodified light chain from the human acceptor antibody. Still alternatively, a compatible light chain may be selected from another human antibody by recourse to the conventional antibody databases. The remainder of the engineered antibody may be derived from any suitable acceptor human immunoglobulin.

The altered antibody thus preferably has the structure of a natural human antibody or a fragment thereof, and possesses the combination of properties required for effective therapeutic use, e.g., treatment of diseases mediated by human receptors containing the $\alpha_v$ subunit, or for diagnostic uses.

It will be understood by those skilled in the art that an altered antibody may be further modified by changes in variable domain amino acids without necessarily affecting the specificity and high affinity of the donor antibody (i.e., an analog). It is anticipated that heavy and light chain amino acids may be substituted by other amino acids either in the variable domain frameworks or CDRs or both. Particularly preferred is the immunological editing of such reconstructed sequences as illustrated in the examples herein.

In addition, the variable or constant region may be altered to enhance or decrease selective properties of the molecules of the instant invention by dimerization, binding to Fc receptors, or the ability to bind and activate complement [see, e.g., Angal et al., 1993, *Mol. Immunol.*, 30:105–108; Xu et al., 1994, *J. Biol. Chem.*, 269:3469–3474; Winter et al., EP 307,434-B], or as described above.

Such antibodies are useful in the prevention and treatment of disorders mediated by these $\alpha_v$-subunit containing integrins, as discussed herein.

VII. Production of Altered Antibodies and Engineered Antibodies

The resulting reshaped and engineered human, humanized and chimeric antibodies of this invention can be expressed in recombinant host cells, e.g., COS, CHO or myeloma cells, by resort to recombinant DNA technology using genetic engineering techniques. The same or similar techniques may also be employed to generate other embodiments of this invention.

Briefly described, a conventional expression vector or recombinant plasmid is produced by placing these coding sequences for the altered antibody in operative association with conventional regulatory control sequences capable of controlling the replication and expression in, and/or secretion from, a host cell. Regulatory sequences include promoter sequences, e.g., CMV promoter, and signal sequences, which can be derived from other known antibodies. Similarly, a second expression vector can be produced having a DNA sequence which encodes a complementary antibody light or heavy chain. Preferably this second expression vector is identical to the first except insofar as the coding sequences and selectable markers are concerned, so to ensure as far as possible that each polypeptide chain is functionally expressed. Alternatively, the heavy and light chain coding sequences for the altered antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The production of the antibody which includes the association of both the recombinant heavy chain and light chain is measured in the culture by an appropriate assay, such as ELISA or RIA. Similar conventional techniques may be employed to construct other altered antibodies and molecules of this invention.

Suitable vectors for the cloning and subcloning steps employed in the methods and construction of the compositions of this invention may be selected by one of skill in the art. For example, the conventional pUC series of cloning vectors, may be used. One vector used is pUC19, which is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

Similarly, the vectors employed for expression of the engineered antibodies according to this invention may be selected by one of skill in the art from any conventional vectors. Preferred vectors include for example plasmids pCD or pCN. The vectors also contain selected regulatory sequences (such as CMV promoters) which direct the replication and expression of heterologous DNA sequences in selected host cells. These vectors contain the above described DNA sequences which code for the engineered antibody or altered immunoglobulin coding region. In addition, the vectors may incorporate the selected immunoglobulin sequences modified by the insertion of desirable restriction sites for ready manipulation.

The expression vectors may also be characterized by genes suitable for amplifying expression of the heterologous DNA sequences, e.g., the mammalian dihydrofolate reductase gene (DHFR). Other preferable vector sequences include a polyadenylation (poly A) signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell transfected with a recombinant plasmid containing the coding sequences of the engineered antibodies or altered immunoglobulin molecules thereof. Host cells useful for the cloning and other manipulations of these cloning vectors are also conventional. However, most desirably, cells from various strains of E. coli are used for replication of the cloning vectors and other steps in the construction of altered antibodies of this invention.

Suitable host cells or cell lines for the expression of the engineered antibody or altered antibody of the invention are preferably mammalian cells such as CHO, COS, fibroblast cells (e.g., 3T3), and myeloma cells. More preferably a CHO or a myeloma cell is used. Human cells may be used, that enable the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., 1989, *Molecular Cloning* (*A Laboratory Manual*), 2nd edit., Cold Spring Harbor Laboratory (New York).

Bacterial cells may prove useful as host cells suitable for the expression of the recombinant Fabs of the present invention [see, e.g., Plückthun, A., 1992, *Immunol. Rev.*, 130:151–188]. The tendency of proteins expressed in bacterial cells to be in an unfolded or improperly folded form or in a non-glycosylated form does not pose as great a concern, because Fabs are not normally glycosylated and can be engineered for exported expression thereby reducing the high concentration that facilitates misfolding. Nevertheless, any recombinant Fab produced in a bacterial cell would have to be screened for retention of antigen binding ability. If the molecule expressed by the bacterial cell was produced and exported in a properly folded form, that bacterial cell would be a desirable host. For example, various strains of *E. coli* used for expression are well-known as host cells in the field of biotechnology. Various strains of *B. subtilis, Streptomyces*, other bacilli and the like may also be employed in this method.

Where desired, strains of yeast cells known to those skilled in the art are also available as host cells, as well as insect cells, e.g. *Drosophila* and Lepidoptera and viral expression systems. See, e.g. Miller et al., 1986, *Genetic Engineering*, 8:277–298 and references cited therein.

The general methods by which the vectors of the invention may be constructed, the transfection methods required to produce the host cells of the invention, and culture methods necessary to produce the altered antibody of the invention from such host cell are all conventional techniques. Likewise, once produced, the altered antibodies of the invention may be purified from the cell culture contents according to standard procedures of the art, including ammonium sulfate precipitation, affinity columns, column chromatography, gel electrophoresis and the like. Such techniques are within the skill of the art and do not limit this invention.

Yet another method of expression of reshaped antibodies may utilize expression in a transgenic animal, such as described in U.S. Pat. No. 4,873,316, incorporated herein by reference.

Once expressed by the desired method, the engineered antibody is then examined for in vitro activity by use of an appropriate assay. Presently conventional ELISA assay formats are employed to assess qualitative and quantitative binding of the altered antibody to the human $\alpha_v\beta_3$ and $\alpha_v\beta_5$ receptors. See, Example 3 below. Additionally, other in vitro assays (such as Example 9) and in vivo animal (such as Examples 13 and 14) models may also be used to verify neutralizing efficacy prior to subsequent human clinical studies performed to evaluate the persistence of the altered antibody in the body despite the usual clearance mechanisms.

As one specific example of the production processes described above, a humanized B9 antibody is generated and expressed as described in detail in Example 11 below.

VIII. Therapeutic/Prophylactic Uses

This invention also relates to a method of treating humans (or other mammals) experiencing symptoms related to diseases which are mediated by receptors such as $\alpha_v\beta_3$, $\alpha_v\beta_5$, $\alpha_v\beta_1$, $\alpha_v\beta_6$, and $\alpha_v\beta_8$, which comprises administering an effective dose of antibodies including one or more of the altered antibodies described herein or fragments thereof. The antibodies of this invention are useful for treating diseases wherein the underlying pathology is attributable to ligand which interacts with an $\alpha_v$-containing receptor, such as the vitronectin receptor. For instance, these antibodies are useful as antitumor, anti-angiogenic, antiinflammatory and anti-metastatic agents, and are particularly useful in the treatment of atherosclerosis, restenosis, cancer metastasis, rheumatoid arthritis, diabetic retinopathy and macular degeneration.

Similarly, these antibodies are useful for treatment of conditions wherein loss of the bone matrix creates pathology. Thus, the instant antibodies are useful for the treatment of osteoporosis, hyperparathyroidism, Paget's disease, hypercalcemia of malignancy, osteolytic lesions produced by bone metastasis, bone loss due to immobilization or sex hormone deficiency.

The therapeutic response induced by the use of the molecules of this invention is produced by the binding to the selected receptor, e.g., $\alpha_v\beta_3$ or the others above mentioned, and thus subsequently blocking disease progression. Thus, the molecules of the present invention, when in preparations and formulations appropriate for therapeutic use, are highly desirable for those persons experiencing disorders mediated by these human $\alpha_v$-containing receptors. For example, longer treatments may be desirable when treating chronic diseases or the like. The dose and duration of treatment relates to the relative duration of the molecules of the present invention in the human circulation, and can be adjusted by one of skill in the art depending upon the condition being treated and the general health of the patient.

The altered antibodies, antibodies and fragments thereof of this invention may also be used alone or in conjunction with other antibodies, particularly human or humanized or human antibodies reactive with other epitopes on the selected integrin receptor as prophylactic agents.

The mode of administration of the therapeutic and prophylactic agents of the invention may be any suitable route which delivers the agent to the host. The altered antibodies, antibodies, engineered antibodies, and fragments thereof, and pharmaceutical compositions of the invention are particularly useful for parenteral administration, i.e., subcutaneously, intramuscularly, intravenously, or intranasally.

Therapeutic and prophylactic agents of the invention may be prepared as pharmaceutical compositions containing an effective amount of the altered antibody of the invention as an active ingredient in a pharmaceutically acceptable carrier. An aqueous suspension or solution containing the antibody, preferably buffered at physiological pH, in a form ready for injection is preferred. The composition for parenteral administration will commonly comprise a solution of the engineered antibody of the invention or a cocktail thereof dissolved in an pharmaceutically acceptable carrier, preferably an aqueous carrier. A variety of aqueous carriers may be employed, e.g., 0.4% saline, 0.3% glycine, and the like. These solutions are sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc.

The concentration of the antibody of the invention in such pharmaceutical formulation can vary widely, i.e., from less than about 0.5%, usually at or at least about 1%, to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg of an engineered antibody of the invention. Desirably the compositions may contain about 50 ng to about 80 mg of antibody, or more preferably, about 5 mg to about 75 mg of antibody according to this invention. Similarly, a pharmaceutical composition of the invention for intravenous infusion could be made up to contain about 250 ml of sterile Ringer's solution, and about 1 to about 75 and preferably 5 to about 50 mg/ml of an engineered antibody of the invention. Actual methods for preparing parenterally administrable compositions are well known or will be apparent to those skilled in the art. Such methods are described in more detail in, for example, Remington's Pharmaceutical Science, 15th ed., Mack Publishing Company, Easton, Pa.

It is preferred that the therapeutic and prophylactic agents of the invention, when in a pharmaceutical preparation, be present in unit dose forms. The appropriate therapeutically effective dose can be determined readily by those of skill in the art. To effectively treat an inflammatory disorder in a human or other animal, one dose of approximately 0.1 mg to approximately 20 mg per 70 kg body weight of a protein or an antibody of this invention should be administered parenterally, preferably i.v. or i.m. (intramuscularly). Such dose may, if necessary, be repeated at appropriate time intervals selected as appropriate by a physician.

The antibodies, altered antibodies or fragments thereof described herein can be lyophilized for storage and reconstituted in a suitable carrier prior to use. This technique has been shown to be effective with conventional immunoglobulins and art-known lyophilization and reconstitution techniques can be employed.

In still an alternative therapeutic regimen, the altered antibodies and monoclonal antibodies of this invention can be used in a combined therapy for the diseases described above with small molecule non-peptide antagonists of the selected integrin receptor. Such small molecule antagonists, the dosages and administration regimens are described in, e.g., International PCT patent publication No. WO96/00730, published Jan. 11, 1996 and International PCT patent publication No. WO96/00574, published Jan. 11, 1996, both incorporated by reference herein. Such combination therapy may involve administering an antibody of this invention to a patient for a short period, i.e., several months to six months, followed by chronic therapeutic treatment with the small molecule antagonists for a longer period of time. In another embodiment, this embodiment of a method of treatment may involve alternating treatment periods of administering immunotherapy with the antibodies of this invention followed by small non-peptide antagonist treatments. Such combined therapeutic methods would employ the same dosages described above for the immunotherapy and the dosages specified in the above-cited applications for the non-peptide therapies.

IX. Diagnostic Uses

The altered antibodies and engineered antibodies of this invention may also be used in diagnostic regimens, such as for the determination of human $\alpha_v$-containing receptor-mediated disorders or tracking progress of treatment of such disorders. As diagnostic reagents, these altered antibodies may be conventionally labeled for use in ELISAs and other conventional assay formats for the measurement of human $\alpha_v$ subunit-containing receptor levels in serum, plasma or other appropriate tissue or the release by human cells in culture. The nature of the assay in which the altered antibodies are used are conventional and do not limit this disclosure.

The following examples illustrate various aspects of this invention including the construction of exemplary engineered antibodies and expression thereof in suitable vectors and host cells, and are not to be construed as limiting the scope of this invention. All amino acids are identified by conventional three letter or single letter codes. All necessary restriction enzymes, plasmids, and other reagents and materials were obtained from commercial sources unless otherwise indicated. All general cloning ligation and other recombinant DNA methodology were as performed in T. Maniatis et al. or Sambrook et al., both cited above.

EXAMPLE 1

Purification of $\alpha_v\beta_3$, $\alpha_v\beta_5$, $\alpha_v\beta_1$ Receptors The human $\alpha_v\beta_3$ protein receptor and other protein receptors were purified from human placenta as follows.

Placentas were frozen immediately after birth, then partially thawed and cut into small chunks which were ground to fine pieces using a commercial meat grinder. Usually five to ten placentas were ground at one time; the pieces were placed into 50 ml centrifuge tubes (6 tubes per placenta) and stored frozen at −20E C until use.

An immunoaffinity column for each integrin was prepared using individual monoclonal antibodies. Anti-$\alpha_v\beta_3$ mAb (LM609) was purified from mouse ascites purchased from Chemicon International, Inc. (Temecula, Calif.). Monoclonal antibodies 23C6 or D12 were purified from hybridoma media. An anti-$\alpha_v\beta_5$ mAb (P1F6) and anti-$\alpha_v\beta_1$ mAb (mAb16) were purchased from Becton Dickinson. LM609 or 23C6 or D12 (50 mg), P1F6 (25 mg), and mAb16 (25 mg) were immobilized on AffiGel® 10 (BioRad) at 5 mg of mAb/ml of resin following the manufacturer's instruction. In order to remove the nonspecific binding proteins, 20 ml of AffiGel® 10 was treated with 1 M Tris HCl pH 7.5 and packed in an Econo Column®. The immobilized mAb's were packed in EconoColumn (BioRad), 10 ml column for LM609 or 23C6 or D12, 5 ml one for P1F6 and 5 ml one for mAb16. The columns were connected in tandem: the first column containing AffiGel® 10 for nonspecific binding, the second column containing $\alpha_v\beta_3$ mAb, the third column containing $\alpha_5\beta_1$ mAb and the fourth column containing P1F6 (the $\alpha_v\beta_5$) mAb. The columns were equilibrated with buffer T (50 mM Tris HCl, pH 7.5, 0.1 M NaCl, 2 mM CaCl, 1% octyl glucoside) in the coldroom.

The ground placenta (9 tubes) was partially thawed and dispersed thoroughly using spatula in buffer T+6% octyl glucoside (final concentration of OG was 3%). The mixture was stored for 5 hours or overnight at 4 C. The bulky solution was transferred to 250 ml centrifuge bottles and centrifuged at 13,000 rpm for one hour. The clear supernatant was transferred to 50 ml centrifuge tubes and centrifuged at 20,000 rpm for one hour. The clear supernatant was combined and loaded with the flow-rate of 30 ml/hour to the columns arranged and pre-equilibrated in buffer T in tandem mode as described above. At the end of loading, the columns were washed with >250 ml of buffer T. Individual columns were then separated and the bound integrins were eluted with 0.2 M acetic acid until pH of the eluate reached <3.0. The eluted integrin solutions were quickly neutralized to >pH 7.0 with 1M Trizma base. The column was also neutralized by washing with buffer T.

The eluted integrin solutions (25 ml) were concentrated to 1 ml using Aquaside® III (Calbiochem) in a dialysis bag of 5000 cut off. The concentrated integrins were dialyzed overnight against buffer T. The final yield was approximately 1 mg for each integrin per placenta.

EXAMPLE 2

Generation of Murine Monoclonal Antibodies

Murine mAbs with anti-$\alpha_v\beta_3$ activity were generated by classical hybridoma technology according to Lane et al, 1986, *Methods in Enzymol.*, 121: 183. Generally, 20–50 Φg of $\alpha_v\beta_3$ receptor was administered ip, sc, and iv to two Balb/c mice. Sera from the immunized animals were tested for their anti-$\alpha_v\beta_3$ binding and neutralizing activity in assays of Examples 3, 4 and 5 below. Mouse spleen from mice showing positive sera was fused with a mouse myeloma cell SP2 according to the procedures of Lane et al, cited above. Seventeen resulting hybridoma cell lines, secreting potential anti-human $\alpha_v\beta_3$ protein antibodies were obtained. These anti-$\alpha_v\beta_3$ mAbs were generated and isolated from culture by conventional methods and tested in assays of the following examples.

Table I is a summary of the data collected from Examples 3–10 below on the murine mAb B9, the murine mAb LM609 of the prior art and other murine mAbs of this invention. The data showed that mAb B9 was a mAb with favorable activity profile. The mAb B9 that functioned adequately in these tests was then selected for humanization as described in Example 11, and further tested in animal models of Examples 13 and 14. The B9 mAb has minimal cross-reactivity with rabbit (not pursuable for in vivo studies), therefore human and primate models of restenosis, angiogenesis or atherosclerosis are applicable for testing efficacy.

TABLE I

|  | Monoclonal antibodies | | | | |
| --- | --- | --- | --- | --- | --- |
| Profiles | LM609 | D12 | 346 | B9 | 387 |
| $\alpha_v\beta_3$ ELISA | + | + | + | + | − |
| $\alpha_5\beta_1$ ELISA | − | − | − | − | − |
| $\alpha_v\beta_5$ ELISA | − | − | − | + | + |
| $\alpha_{IIb}\beta_3$ ELISA | − | − | + | − | − |
| Specificity | $\alpha_v\beta_3$ | $\alpha_v\beta_3$ | $\beta_3$ | $\alpha_v\beta_3$ $\alpha_v\beta_5$ | $\alpha_v\beta_5$ |
| Neutralization | 3+ | 3+ | +/− | 5+ | − |
| Immunohistology | 3+ | 3+ | 2+ | 5+ | 3+ |
| Inhibition Adhesion. HEK293 ($V_n$) | + | + | −* | 2+ | − |
| Echistatin binding HEK293 | 3+ | 3+ | − | 5+ | − |
| FLOW Hu-SMC | + | + | + | 2+ | ND |
| FLOW R-SMC | + | + | +/+ | +/− | ND |
| Inhib (%) R-SMC (50Φg/ml) | 43 | 66 | 75 | − | − |

EXAMPLE 3

ELISA Binding Assay with $\alpha_v\beta_3$ and $\alpha_v\beta_5$

Binding of the various antibody constructs to purified human placenta $\alpha_v\beta_3$ receptor protein and $\alpha_v\beta_5$ receptor protein as antigens (receptor either bound to the plate or to the beads via biotin-avidin) was measured in a standard solid phase ELISA.

Antigen diluted in 0.1 M $CO_3$ pH 9.2 was adsorbed onto polystyrene round-bottom microplates (Dynatech®, Immunolon II) for 18 hours. Wells were then washed one time with phosphate buffered saline (PBS) containing 0.05% Tween® 20. Antibodies (50 Φl/well) were diluted to varying concentrations in PBS/0.05% Tween® 20 and added to the antigen coated wells for two hours at room temperature.

Plates were washed four times with PBS containing 0.05% Tween® 20, using a Titertek® 320 microplate washer, followed by addition of HRP-anti-mouse IgG (100 μl/well) diluted 1:10,000.

After washing five times, o-phenylenediamine dihydrochloride (OPD) (1 mg/ml) was added and plates were incubated an additional 10 minutes. The reaction was stopped by addition of 0.1M NaF and absorbance read at 450 nm using a Dynatech® MR 7000 ELISA reader.

EXAMPLE 4

Elisa Binding Assays with $\alpha_v\beta_3$, $\alpha_v\beta_1$, and $\alpha_{IIb}\beta_3$ and $\alpha_v\beta_5$ MAbs positive in the assay of Example 3 were screened using the same protocols except that the antigen was another human receptor, $\alpha_v\beta_1$ or $\alpha_{IIb}\beta_3$. These assays were run to determine selectivity for the heterodimeric antigen $\alpha_v\beta_3$ and $\alpha_v\beta_5$ as opposed to selectivity for a β subunit only. The results of these assays are reported in Table I above for all mAbs of Example 2 and for LM609.

EXAMPLE 5

Neutralization ELISA Assay

Vitronectin receptors $\alpha_v\beta_3$ and $\alpha_v\beta_5$ (0.2 μg/well), purified from human placenta, was added to 96-well ELISA plates (Corning, New York, N.Y.). The plates were incubated overnight at 4°C. At the time of experiment, the wells were aspirated and incubated in 0.1 ml of Buffer A (50 mM Tris, 100 mM NaCl, 1 mM CaCl$_2$, 1 mM MgCl$_2$, 1 mM MnCl$_2$, pH 7.4) containing 3% bovine serum albumen (BSA) for 1 hour at room temperature to block nonspecific binding. After aspirating the blocking solution, various concentrations of mAbs were added to the wells and followed by the addition of 5 nM biotinylated fibrinogen in 0.1 ml of Buffer A containing 0.1% BSA. The plates were incubated for 1 hour at room temperature.

Following the incubation the wells were aspirated completely and washed twice with 100 μl of binding buffer. Bound fibrinogen was quantitated by addition of 0.1 ml of an anti-biotin antibody conjugated to alkaline phosphatase (1:2000 dilution, Sigma), followed by washing twice with binding buffer and the addition of 100 μl of the substrate p-nitrophenyl phosphate prepared daily according to the manufacturer's instructions (alkaline phosphate substrate kit, Bio-Rad). The kinetics of color development were followed using a microtiter plate reader.

This assay detected inhibition of binding between purified $\alpha_v\beta_3$ receptor and its ligand, fibronectin. The results of these assays are reported in Table I above for all mAbs of Example 2 and for LM609.

EXAMPLE 6

Flow Cytometry

To characterize several of the murine mAbs obtained as described above with the known murine mAb LM609, this assay was performed to detect binding to the native cell surface receptor and species cross-reactivity.

Briefly described, cells are washed in 10 ml cold PBS and resuspended in cold PBS to give between $1\times10^7$ to $2\times10^7$ cells/ml. Aliquots of 0.1 ml/well are added to 96 well "V" bottom plate. Then, 25 μl of primary antibody is added. The plates are shaken for five minutes, and then incubated on ice for 25 minutes. The plates are centrifuged for five minutes and flicked. Thereafter the contents of each well is resuspended in 50 μl cold PBS, and again centrifuged and flicked. The wash is repeated and the contents resuspended to 50 μl cold PBS. Fluorescein isothiocyanate (FITC)-labelled secondary antibody (50 μl) is added to each well. The plates are shaken for five minutes, and incubated on ice in the dark for 20 minutes. One μL of propidium iodide (PI) (1 mg/ml)/PBS is added to a final concentration of 10 μg/ml (1 μg in 0.1 ml). Incubation is continued for five minutes, followed by centrifuging and washing twice in cold PBS.

Cells are resuspended to 0.1 ml cold PBS, and transfered to 12×75 clear Falcoln tubes. Volume is adjusted to 1 ml, and cells are held cold in the dark until read by FLOW.

The secondary antibody:Goat Anti-Mouse IgG,M,A is labelled with FITC 1:25/PBS-0.2% BSA-0.1% NaN$_3$ (Sigma F1010 lot #045H8822) and hold cold in the dark until read by FLOW.

The results of these assays are reported in Table I and show a clear indication that B9 binds to cells expressing $\alpha_v\beta_3$ and $\alpha_v\beta_5$. Flow cytometry using human smooth muscle cells (SMC) indicated that mAb B9 has great capacity to bind to a native receptor on the cell surface.

EXAMPLE 7

Immunohistology

Immunohistology was performed on tissues expressing high levels of receptors, such as human osteoclastoma. Data from immunohistology (human osteoclastoma) showed that B9 has superior detection capability. See Table I. B9 detects human, baboon and rabbit $\alpha_v\beta_3/\alpha_v\beta_5$ on cells and human tissue.

EXAMPLE 8

BIAcore® to Determine mAb Affinity to the Receptors

A BIAcore® analysis (Pharmacia) was performed to measure binding affinity of mAb B9 (6 nM) with immobilized $\alpha_v\beta_3$ and $\alpha_v\beta_5$. The interactions of these receptors with B9 were studied using BIAcore® technology by immobilization of the receptors onto the sensor surface, and passing solutions of the mAb over this surface. Descriptions of the instrumentation and sensor surfaces are described in [Brigham-Burke, Edwards and O'Shannessy, 1992, *Analytical Biochem.*, 205:125–131]. The receptors was immobilized by inserting it into a phospholipid vesicle and producing a hybrid bilayer membrane on a hydrophobic sensor surface. A more complete description of generation of hybrid bilayer membranes on BIAcore® sensor surfaces is provided in Plant et al, 1995, *Analyt. Biochem.*, 226:342–348. Samples of the mAb were passed over this surface and the rates at which they bound and then dissociated from the surface were measured and analyzed using software provided with the instrument.

Table II provides this data. Kinetic rate constants and calculated affinity constant ($K_D$) were derived from the analysis of three mAb concentrations (100, 25, 6 nM) performed in triplicate. The Biacore® data showed that the binding affinity ($K_D$) of B9 is approximately 5 times higher than that for the D12 Mab for the $\alpha_v\beta_3$ receptor.

TABLE II

| mAb | Calc. $K_D$ (nM) | |
| --- | --- | --- |
| | Anti-$\alpha_v\beta_3$ | Anti-$\alpha_v\beta_5$ |
| Murine B9 | 0.29 | 0.11 |
| Murine D12 | 1.3 | — |

In a second format of the BIAcore® analysis, Protein A was employed to immobilize the mAbs onto the sensor surface and then samples of the receptor proteins were passed over this surface and the rates at which they bound and then dissociated from the surface were measured and analyzed using software provided with the instrument. Table III provides data which permits the evaluation of different humanized B9 constructs for their binding activity against $\alpha_v\beta_3$ receptor. The humanized B9 mAbs in Table III are characterized by the heavy chain from IgG1, except for B9HL1G4, which has a heavy chain from IgG4. Three different light chains are represented by L1, L2, and L3. The anti-$\alpha_v\beta_3$ mAb (D12IgG1) was included for comparison. The $k_{ass}$ (rate of association) and the $K_{diss}$ (rate of dissociation) are measurements which calculate the affinity of the mAbs against the $\alpha_v\beta_3$ receptor ($K_D$ in nM). This Biacore® data indicates that the B9 mAbs have a higher affinity for the $\alpha_v\beta_3$ receptor than does the D12 in Ab.

TABLE III

| mAb | $k_{ass}(M^{-1}s^{-1})$ | $k_{diss}(s^{-1})$ | calc. $K_D$ (nM) |
| --- | --- | --- | --- |
| B9HL1G1 | 1.7 × 10$^5$∀0.2 | 1.4 × 10$^{-3}$∀0.6 | 8.2 |
| B9HL1G4 | 1.7 × 10$^5$∀0.3 | 9.1 × 10$^{-4}$∀4.1 | 5.4 |
| B9HH1G1/HL3K | 1.6 × 10$^5$∀0.3 | 1.1 × 10$^{-3}$∀0.6 | 6.9 |
| B9HL2G1 | 1.9 × 10$^5$∀0.2 | 1.3 × 10$^{-3}$∀0.2 | 7.1 |
| D12IgG1 | 3.7 × 10$^4$∀1.2 | 3.8 × 10$^{-4}$∀1.0 | 10 |

EXAMPLE 9

Vascular Smooth Muscle Cell (SMC) Migration Assay

Smooth muscle cell (SMC) migration from the media into the wound area to initiate growth of the neointima is an essential remodeling response following vascular injury. Inhibition of SMC migration attenuates neointima formation. Vascular SMC migration is mediated via the human $\alpha_v\beta_3$ receptor, which is expressed in VSMC and upregulated following vascular injury. Osteopontin, a ligand of the human $\alpha_v\beta_3$ receptor, is upregulated following angioplasty and promotes VSMC migration via the integrin. This experiment was performed to demonstrate the ability of an antibody to human $\alpha_v\beta_3$ to inhibit VSMC migration in vitro.

Human aortic smooth muscle cells were used. Cell migration was monitored in a Transwell cell culture chamber by using a polycarbonate membrane with pores of 8 μm (Costar). The lower surface of the filter was coated with vitronectin or osteopontin. Cells were suspended in Difco's minimal essential medium (DMEM) supplemented with 0.2% BSA at a concentration of 2.5–5.0×10$^6$ cells/mL, and were pretreated with test antibody at various concentrations for 20 minutes at 20E C. The solvent alone was used as control. 0.2 mL of the cell suspension was placed in the upper compartment of the chamber. The lower compartment contained 0.6 mL of DMEM supplemented with 0.2% BSA. Incubation was carried out at 37E C in an atmosphere of 95% air/5% $CO_2$ for 24 hours.

After incubation, the non-migrated cells on the upper surface of the filter were removed by gentle scraping. The filter was then fixed in methanol and stained with 10% Giemsa stain. Migration was measured either by a) counting the number of cells that had migrated to the lower surface of the filter or by b) extracting the stained cells with 10% acetic acid followed by determining the absorbance at 600 nM.

Inhibition of human SMC migration showed that B9 is more potent than D12 and LM609. See Table I.

EXAMPLE 10

HEK293 Cell Adhesion to Determine Inhibition of Adhesion

Human embryonic kidney cells (HEK293 cells) were obtained from ATCC (Catalog No. CRL 1573). Cells were grown in Earl's minimal essential medium (EMEM) medium containing Earl's salts, 10% fetal bovine serum (FBS), 1% glutamine and 1% Penicillin-Streptomycin.

A 3.2 kb EcoRI-KpnI fragment of the $\alpha_v$ subunit and a 2.4 kb XbaI-XhoI fragment of the $\beta_3$ subunit were inserted into the EcoRI-EcoRV cloning sites of the pCDN vector which contains a CMV promoter and a G418 selectable marker by blunt end ligation. For stable expression, 80×10$^6$ HEK 293 cells were electrotransformed with $\alpha_v+\beta_3$ constructs (20 Φg DNA of each subunit) using a Gene Pulser® [P. Hensley et al., 1994, J. Biol. Chem., 269:23949–23958] and plated in 100 mm plates (5×10$^5$ cells/plate). After 48 hours, the growth medium was supplemented with 450 Φg/ml Geneticin (G418 Sulfate, GIBCO-BRL, Bethesda, Md.). The cells were maintained in selection medium until the colonies were large enough to be assayed.

Corning 96-well ELISA plates were precoated overnight at 4E C with 0.1 ml of human vitronectin (0.2 Φg/ml in RPMI medium). At the time of the experiment, the plates were washed once with RPMI medium and blocked with 3.5% BSA in RPMI medium for 1 hour at room temperature. Transfected 293 cells were resuspended in RPMI medium, supplemented with 20 mM Hepes, pH 7.4 and 0.1% BSA at a density of 0.5×10$^6$ cells/ml. 0.1 ml of cell suspension was added to each well and incubated for 1 hour at 37E C, in the presence or absence of various $\alpha_v\beta_3$ antagonists. Following incubation, 0.025 ml of a 10% formaldehyde solution, pH 7.4, was added and the cells were fixed at room temperature for 10 minutes. The plates were washed 3 times and 0.2 ml of RPMI medium and the adherent cells were stained with 0.1 ml of 0.5% toluidine blue for 20 minutes at room temperature.

Excess stain was removed by extensive washing with deionized water. The toluidine blue incorporated into cells was eluted by the addition of 0.1 ml of 50% ethanol containing 50 mM HCl. Cell adhesion was quantitated at an optical density of 600 nm on a microtiter plate reader (Titertek® Multiskan MC, Sterling, Va.).

The neutralization of receptor inhibition of cell adhesion showed that B9 is superior to D12 and LM609 in inhibiting cell adhesion (see Table I; see also).

EXAMPLE 11

Generating Humanized B9

A. Generating Heavy and Light Chain Variable Regions

A humanization strategy was adopted to obtain a maximally humanized Mab that fully retained antigen binding affinity and avidity. The cDNA of the variable heavy chain (VH) and variable kappa light chain (Vk) were cloned and sequenced. The sequence of VHB9 is shown in FIG. 1A [SEQ ID NOS. 1, 2 and 38] (with the CDRs in bold type and underlined) and the sequence of VkB9 is shown in FIG. 2A [SEQ ID NOS 6, 7 and 39] (with the CDRs in bold type and underlined).

Following cDNA cloning and sequence analysis, VHB9 and VkB9 were found to be most similar to Kabat VH subgroup I (FIG. 1B; [SEQ ID NO. 3]) and Vk subgroup I (FIG. 2B; [SEQ ID NO. 8]), respectively. Humanized VH and VL regions were synthesized by combining the framework regions of the human V region subgroup consensus sequences together with the CDR regions of B9.

Molecular modeling of B9 using known crystal structures reveals certain VH and VL framework residues that can make contact with CDR residues, and thereby influence their conformation. Such framework residues can therefore directly contribute to the formation of a particular antigen specificity and associated binding affinity. Eight such murine VH framework residues (indicated by asterisks in FIG. 1C. [SEQ ID NOS. 4 and 5]) and one murine Vk framework residue (indicated by asterisks in FIG. 2C [SEQ ID NOS. 9, 10 and 40]) were introduced into the human consensus framework regions, resulting in B9 HZHC1-0 (FIG. 1C; [SEQ ID Nos. 4 and 5]) and B9 HZLC1-0 (FIG. 2C; [SEQ ID NOS. 9, 10 and 40]).

B. B9 Mab Heavy and Light Chain cDNA Sequence Analysis

N-terminal amino acid microsequencing was performed on B9 heavy and light chains. The N-terminal VH sequence, QVQLQQSGAELMKPGA [SEQ ID NO:16] and Vk sequence, DIQMTQTTSSLXAXL [SEQ ID NO: 17] were used to design degenerate PCR primers that could direct PCR amplification of the unknown VH and Vk regions, respectively. These degenerate primers were designed such that the amplified V-regions would nevertheless encode authentic N-termini.

B9 hybridoma cell total RNA was purified by using TRIzol Reagent® (Life Technologies Cat. # 15596-026) according to the manufacturer's protocol. RNA was precipitated with isopropanol and dissolved in distilled water. One hundred ng of RNA was reverse transcribed with a RT-PCR kit per the manufacturer's instructions (Boehringer Mannheim Cat. No. 1483-188) using oligo-dT for priming. For the heavy chain, PCR amplification of the RNA/DNA hybrid was carried out for 25 cycles using a mouse $IgG_1$ CH1 reverse primer SBA3434: 5' AGG GGC CAG TGG ATA GAC 3' [SEQ ID NO. 18] and a degenerate forward primer based on the VH N-term protein sequence SBA3204:5' GCT ACC GGT GTC CAC TCC CAA GTN CA(A/G) CTN CA(A/G) CA 3' [SEQ ID NO. 19].

Similarly, for the light chain, PCR amplification of the RNA/DNA hybrid was carried out for 25 cycles using a mouse kappa reverse primer SBA0352: 5' GCA CCT CCA GAT GTT AAC TGC 3' [SEQ ID NO. 20] and a degenerate forward primer based on the Vk N-terminal protein sequence SBA9258: 5' GCT ACC GGT GTC CAC TCC GA(C/T) AT(A/C/T) CA(A/G) ATG ACN CA 3' [SEQ ID NO. 21]. The PCR DNA was analyzed on a 0.8% agarose gel. PCR inserts of the appropriate size, ~400 bp, were sequenced by a modification of the Sanger method.

The sequence of 5 heavy and 5 light chain clones were compared to generate a consensus B9 heavy chain variable region sequence (FIG. 1C; [SEQ ID NOS. 4 and 5]) and consensus 3G9 light chain variable region sequence (FIG. 2C; [SEQ ID NOS. 9, 10 and 40]). The CDR's are shown in bold. The first 17 bases of DNA sequence for the heavy and light chains are PCR primer generated, however the translated protein sequence is exact.

C. Humanization of B9

The humanized B9 antibody as described herein consists of the synthetic, consensus heavy chain B9 HZHC1-0 [SEQ ID NO. 4] of FIG. 1C, and the synthetic, consensus light chain B9 HZLC1-0 [SEQ ID NO. 9] of FIG. 2C. The antibody was constructed as follows.

i. Construction of B9 HZHC1-0

A synthetic humanized heavy chain variable region was designed using human heavy chain subgroup I consensus sequence frameworks as defined by Kabat and the murine B9 heavy chain CDRs described previously. Eight murine framework amino acids substitutions which might influence CDR presentation were introduced (see asterisks in FIG. 1C). Four overlapping synthetic oligonucleotides were synthesized with the following sequences:

Oligo SBB0187: 5=TTT TTA ACC GGT GTC CAC TCC CAA GTT CAG CTT GTA CAG TCT GGA GCT GAG GTG AAG AAG CCT GGG GCC TCA GTG AAG GTA TCC TGC AAG GCT TCT GGC TAC ACA TTC AGT AGC TAC TGG 3=[SEQ ID NO: 32]

Oligo SBB0188: 5=CTT CTC ATT GTA GTT AGT ATT ACC ACT TCT AGG TAA AAT CTC TCC AAT CCA CTC AAG GCC TTG TCC AGG GGC CTG CTT TAC CCA CTC TAT CCA GTA GCT ACT GAA TGT GTA GCC 3=[SEQ ID NO: 33]

Oligo SBB0189: 5=GGT AAT ACT AAC TAC AAT GAG AAG TTC AAG GGC AAG GCC ACA TTC ACT GCA GAT ACA TCC ACC AGC ACA GCC TAC ATG GAA CTC AGC AGC CTG AGA TCT GAG GAC ACT GCC GTC 3=[SEQ ID NO: 34] and Oligo SBB 0190: 5=TCT GCT GGG GCC CTT GGT ACT AGC TGA GGA GAC GGT GAC TAA GGT TCC TTG ACC CCA GTA GTC CAT AGA GCC CCT GAC GCC GCG ACT TGA ACA GTA ATA GAC GGC AGT GTC CTC AGA TCT CAG 3=[SEQ ID NO: 35].

When annealed and extended, the oligonucleotide sequences code for the V-region amino acids of the humanized heavy chain (see FIG. 3; [SEQ ID NOS. 11, 12 and 41]). This synthetic gene was PCR amplified with primers SBB0191: 5=TTA ACC GGT GTC CAC TCC CAA GTT CAG 3=[SEQ ID NO: 36] and SBB0192: 5=GCT GGG GCC CTT GGT ACT AGC TGA GGA 3=[SEQ ID NO: 37] and ligated into the pCR2000 cloning vector (TA cloning Kit, Invitrogen, Cat. No. K2000-01), and isolated after a AgeI, ApaI restriction digest.

This DNA fragment was ligated into the vector pCDH-CAGE which had previously been restriction digested with AgeI and ApaI. pCDHCAGE is a variant of the plasmids pCDN [A. Nambi et al., 1994, *Mol. Cell. Biochem.*, 131: 75–85] and F9 HZLCl-1-pCN [International patent publication WO94/05690]. These pCDN variant plasmid vectors contain, in general, a beta lactamase gene, a SV40 origin of replication, a cytomegalovirus promoter sequence, a selected humanized light chain, a poly A signal for bovine growth hormone, a beta globin promoter, a neomycin resistance gene, and another BGH sequence poly A signal in a pUC19 background. pCDHCAGE further contains the CAMPATH immunoglobulin leader sequence in which a unique AgeI site had been introduced at the 3' end, a linker sequence followed by uninterrupted heavy chain coding sequences commencing at a unique ApaI site at the 5' end of the human CH1 region through to the end of the human CH3 region. The resulting gene codes for a complete humanized heavy chain, comprising the initiation codon, the CAMPATH leader peptide, the humanized VH region, and a complete IgG, constant region. This expression construct is called pCDB9 HZHC1-0, and when cultured in a suitable host cell, produces a complete human IgG, chain with the humanized B9 heavy chain V-region B9 HZHC1-0 (FIG. 1C; [SEQ ID NOS. 4 and 5]).

ii. Construction of B9 HZLCI—O

A synthetic humanized light chain variable region was designed using a human light chain subgroup I variable region consensus framework as described by Kabat and the B9 light chain CDRs as described previously. One murine framework amino acid substitution which might influence CDR presentation was introduced (see asterisk in FIG. 2C; [SEQ ID NOS. 9, 10 and 40]). Four overlapping synthetic oligonucleotides were generated with the following sequences:

SBB0030: 5' TTT TTG GCT ACC GGT GTC CAC TCC GAT ATT CAG ATG ACC CAG TCT CCA TCC TCC CTG TCT GCC TCT GTG GGA GAC AGA GTC ACC ATC ACT TGC AGG 3' [SEQ ID NO.22];

SBB0031: 5' TAA TGT TGA TGT GTA GTA GAT CAG AAG CTT AGG AGC TTT ACC TGG TTT CTG CTG ATA CCA GTT TAA AAA ATT GCT AAT GTC CTG ACT TGA CCT GCA AGT GAT GGT GAC TCT GTC 3' [SEQ ID NO.23];

SBB0032: 5'CTG ATC TAC TAC ACA TCA ACA TTA CAC TCA GGA GTC CCA TCA AGG TTC AGT GGC AGT GGG TCT GGA ACA GAT TAT ACT CTC ACC ATT AGC AGC CTG CAG 3' [SEQ ID NO.24];

SBB0033: 5' TGT ACG GGT ACC TCC ACC GAA CGT CCA AGG AAG CGT ATT ACC CTG TTG GCA ATA GTA AGT GGC AAA ATC TTC TGG CTG CAG GCT GCT AAT GGT GAG 3' [SEQ ID NO.25].

When annealed and extended, the oligonucleotide sequence codes for the amino acids of the humanized B9 Vk region, B9 HZLC1-0 (see FIG. 4 [SEQ ID NOS. 13, 14 and 42]).

This synthetic Vk region was then PCR amplified using primers SBB0034: 5' TTT TTG GCT ACC GGT GTC CAC TCC GAT ATT CAG 3' [SEQ ID NO. 26] and SBB0035: 5' ACG GGT ACC TCC ACC GAA CGT CCA AGG 3' [SEQ ID NO. 27] and ligated into the pCR2000 cloning vector (TA cloning Kit, Invitrogen, Cat. No. K2000-01), and isolated after a AgeI, KpnI restriction digest.

This DNA fragment was ligated into the vector pCNL-CAGE which had previously been restriction digested with AgeI and KpnI. pCNLCAGE is a variant of the plasmids pCDN [A. Nambi et al., 1994, *Mol. Cell. Biochem.*, 131: 75–85] and F9HZLC1-1-pCN [International patent publication WO94/05690]. These pCDN variant plasmid vectors contain, in general, a beta lactamase gene, a SV40 origin of replication, a cytomegalovirus promoter sequence, a selected humanized light chain, a poly A signal for bovine growth hormone, a beta globin promoter, a neomycin resistance gene, and another BGH sequence poly A signal in a pUC19 background. pCNLCAGE further contains the CAMPATH immunoglobulin leader sequence in which a unique AgeI site had been introduced at the 3' end, a linker sequence followed by uninterrupted light chain coding sequences commencing at a unique KpnI site in the middle of the human Jk region through to the end of the human Ck region (i.e., the light chain constant region of the k isotype, as opposed to the lambda isotype). The resulting gene codes for a complete humanized light chain, comprising the initiation codon and the end of the Ck domain. This expression construct is called pCNB9 HZLC1-0, and when cultured in a suitable host cell, produces a complete human k chain with the humanized B9 light chain V-region B9 HZLC1-0 (FIG. 2C; [SEQ ID NOS. 9 and 10]).

D. Expression of Humanized Antibody in Mammalian Cells

The heavy chain vector pCDB9 HZHC1-0 and light chain vector pCNB9HZLC1-0 described above were used to produce antibody HuB9 in COS calls and CHO cells.

For initial characterization, the humanized HuB9 heavy and light chains were expressed in COS cells essentially as described in Current Protocols in Molecular Biology (edited by F. M. Ausubel et al., 1988, John Wiley & Sons, vol. 1, section 9.1). Briefly described, the COS cells were co-transfected with 10 Φg of each plasmid. On day 1 after the transfection, the culture growth medium was replaced with a serum-free medium which was changed on day 3. The serum-free medium was a proprietary formulation, but satisfactory results are obtained using DMEM supplemented with ITS™ Premix® (insulin, transferrin, selenium mixture—Collaborative Research, Bedford, Mass.) and 1 mg/ml BSA. The mAb was isolated and prepared from the day 3+day 5 conditioned medium by standard protein A affinity chromatography methods (e.g., as described in Protocols in Molecular Biology) using, for example, Prosep A affinity resin (Bioprocessing Ltd., UK).

The humanized B9 was expressed as a γ1, kappa molecule in transiently transfected COS cells. The supernatants of this culture were found to bind to the $\alpha_v\beta_3$ receptor and the $\alpha_v\beta_5$ receptor in both ELISA and BIAcore® assays described above.

To produce larger quantities of the HuB9 mAbs (100–200 mgs), the plasmids were introduced into a proprietary CHO cell system, the CHO-E1a cell line. This cell line supplies larger quantities of mAbs (approximately 10 mg of each) and enables testing of the activity profile of both chimeric and humanized antibodies. However, similar results will be obtained using dhfr⁻ CHO cells as previously described [P. Hensley et al., cited above]. Briefly, a total of 30 Φg of linearized plasmid DNA (15 μg each of the heavy or light chain plasmids) is electroporated into $1 \times 10^7$ cells. The cells are initially selected in nucleoside-free medium in 96 well plates. After three to four weeks, media from growth positive wells is screened for human immunoglobulin using the ELISA assay of Example 3. The highest expressing colonies are expanded and selected in increasing concentrations of methotrexate for amplification of the transfected vectors. The antibody is purified from conditioned medium by standard procedures using protein A affinity chromatography (Protein A sepharose, Pharmacia) followed by size exclusion chromatography (Superdex® 200, Pharmacia).

The concentration and the antigen binding activity of the eluted antibody are measured by the ELISA assays of Examples 3 and 4. The antibody containing fractions are pooled and further purified by size exclusion chromatography.

EXAMPLE 12

Construction of B9HZREI and Other Humanized Variants

A second construct has a light chain based on the human REI consensus framework to provide an alternative light chain in the event of unstable expression in humanized B9 production cell lines. This variant differs from B9HZLC1-0 by only two conservative amino acid interchanges, L73F and F83I (numbering convention of Kabat).

Briefly described, a humanized kappa light chain was designed based on a modified human REI kappa chain framework of FIG. 5 [SEQ ID NO. 15] and the B9 Vk CDRs described previously. As for B9 HZLC1-0 only one donor (B9) framework residue was introduced, at a position identified in modeling experiments which might influence CDR presentation. Site directed mutagenesis was used to incorporate the L73F and F83I amino acid interchanges into the B9 HZLC1-0 intermediate (FIG. 4 [SEQ ID NOS 13, 14 and 42]). Following AgeI-KpnI digestion, the REI based fragment was cloned into AgeI-KpnI digested pCNLCAGE as described for B9 HZLC1-0. The resulting humanized V region was that of B9 HZLCREI of FIG. 6 [SEQ ID NOS: 28, 29 and 43].

A third B9 humanized light chain variant was created that differed from B9 HZLC1-0 by the single amino interchange K103N (numbering convention of Kabat). This variant was created by site directed mutagenesis of the B9 HZLC1-0 intermediate (FIG. 4 [SEQ ID NOS 13, 14 and 42]) and cloned into pCNLCAGE as described above. The resulting humanized V region was that of B9 HZLCI-1 of FIG. 7 [SEQ ID NOS: 30, 31 and 44].

An IgG4 isotypic variant of B9 HZHC1-0 was created by cloning the AgeI-ApaI fragment of the B9 HZHC1-0 intermediate synthetic heavy chain (FIG. 3; [SEQ ID NOS: 11, 12 and 41]) into an AgeI-ApaI digested IgG$_4$ expression vector. This vector, pCDHCAGEG4, is a derivative of pCDHCAGE in which the IgG$_4$C-region replaces the IgG$_1$ C-region sequences. The resulting construct encodes a complete IgG$_4$ heavy chain with ie B9HZHC1-0 variable region.

EXAMPLE 13

SCID Model of Cancer

The SCID model, in which human skin is grafted on the SCID mouse, which serves as a source of angiogenic neovascularization, and subsequently accepts human tumor (tumor growth supported by human vasculature) is utilized for efficacy testing of the B9 mAbs and HuB9 antibodies. Inhibition of tumor growth indicates that B9 mAbs (human anti-$\alpha_v\beta_3$ and anti-$\alpha_v\beta_5$ positive, murine anti-$\alpha_v\beta_3$ negative) play a role in the inhibition of $\alpha_v\beta_3$ dependent angiogenesis.

Antibodies of this invention are also tested for in vivo activities in other mammalian models of cancer metastasis, rheumatoid arthritis and atherosclerosis, e.g., baboon models.

EXAMPLE 14

Mouse Tumor Xenograft Model with HT29

The SCID mouse xenograft model with HT29 human tumor cells showed that B9 mAbs have anti-tumor activity. The activity of the B9 mAbs was evaluated by modifying the model. In the first experiment, the cells were injected i.p. and the treatment was also i.p. The effect of the mAbs on the tumor growth showed that the tumor size of the treated animals was 6.5× smaller. See FIG. 8.

Figure 9:
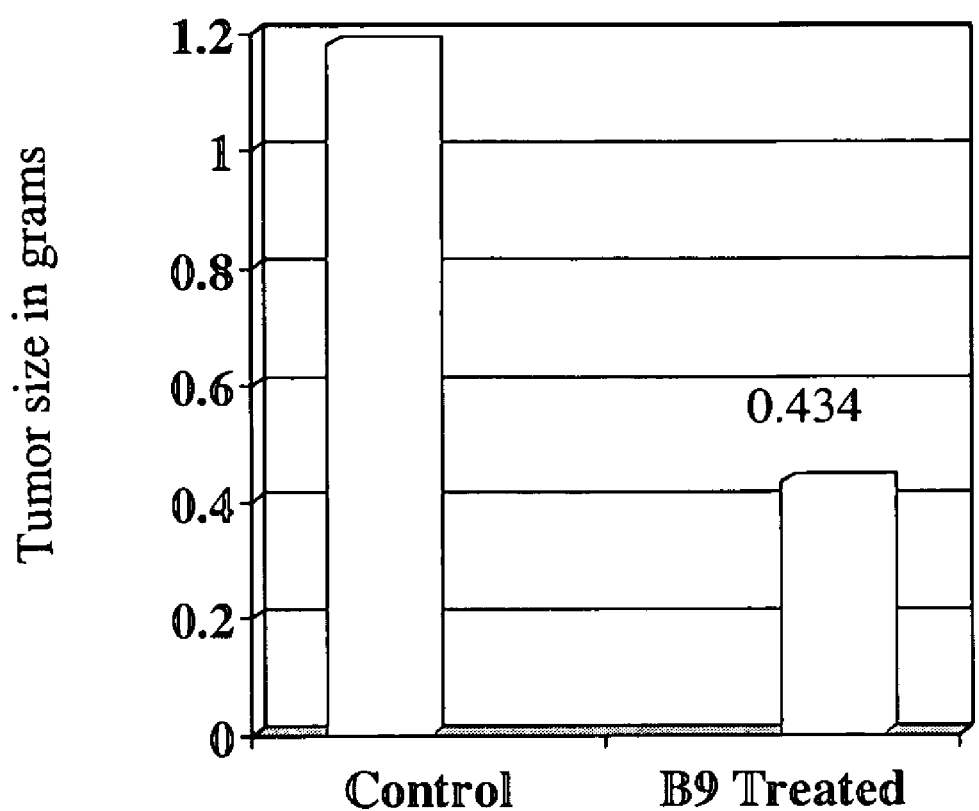
FIG. 9 is a graph showing the results of the mouse tumor xenograft model with HT29 assay of Example 14, with the cells injected s.c.

In the second experimental model, the cells were injected subcutaneously. The treatment was by i.p. injection, twice a week at 1 mg/dose of B9 mAbs (n=8). The results indicated that the animals without the treatment had 2–3 times larger tumors than the treated animals with the B9 mAbs. The s.c. tumor is a more vigorous system than the i.p. tumor described above. See FIG. 9.

Immunohistology on the tumors from both models showed that the untreated control tumors were B9 positive (direct labelling with biotinylated B9). The tumors from the treated mice were B9 negative.

EXAMPLE 15

Human Aorta Ring Angiogenesis Model

This in vitro assay is performed to measure anti-angiogenic activity. Human thoracic aorta is extracted and sectioned into roughly 1 mm sections and placed into 24 well culture plates that contain a three-dimensional matrix. Endothelial cells form vessel-like capillaries branching off from the aorta. B9 mAbs are introduced into this system and their effect on angiogenesis is studied.

The results of Examples 3 through 10 establish that the B9 and HuB9 antibodies have potent anti-receptor activity in vitro and are likely to show prophylactic and therapeutic efficacy in vivo in animal models. Thus, the B9 and HuB9 antibodies are candidates for therapeutic, prophylactic, and diagnostic application in man.

It will be clear that the invention may be practiced otherwise than as particularly described in the foregoing description and examples. Numerous modifications and variations of the present invention are possible in light of the above teachings and, therefore, are within the scope of the appended claims. All documents cited above are incorporated herein by reference.

What is claimed is:

1. An isolated nucleic acid molecule comprising a nucleic acid sequence chosen from the group consisting of:
   (a) a nucleic acid sequence encoding an immunoglobulin heavy chain polypeptide comprising a heavy chain variable region comprising complementarity determining regions (CDRs) having the amino acid sequences shown in residues 31–35, 50–66 and 99–107 of SEQ ID NO: 2, wherein said polypeptide when operatively combined with an immunoglobulin light chain polypeptide comprising a light chain variable region comprising CDRs having the amino acid sequences shown in residues 24–34, 50–56 and 89–97 of SEQ ID NO: 7 forms an antigen-combining region that binds the $\alpha_v$ subunit of $\alpha_v\beta_3$ and $\alpha_v\beta_5$; and
   (b) a nucleic acid sequence that is fully complementary to the entirety of said nucleic acid sequence encoding an immunoglobulin heavy chain polypeptide.

2. The isolated nucleic acid molecule of claim 1, wherein said immunoglobulin heavy chain polypeptide comprises the amino acid sequence shown in SEQ ID NO: 2.

3. The isolated nucleic acid molecule of claim 2 having the sequence shown in SEQ ID NO: 1.

4. The isolated nucleic acid molecule of claim 1, wherein said immunoglobulin heavy chain polypeptide comprises the amino acid sequence shown in SEQ ID NO: 5.

5. The isolated nucleic acid molecule of claim 4 having the sequence shown in SEQ ID NO: 4.

6. A recombinant plasmid comprising the nucleic acid sequence of a nucleic acid molecule of claim 1.

7. An isolated host cell comprising the plasmid of claim 6.

8. An isolated nucleic acid molecule comprising a nucleic acid sequence chosen from the group consisting of:
   (a) a nucleic acid sequence encoding an immunoglobulin light chain polypeptide comprising a light chain variable region comprising complementarity determining regions (CDRs) having the amino acid sequences shown in residues 24–34, 50–56 and 89–97 of SEQ ID NO: 7, wherein said polypeptide when operatively combined with an immunoglobulin heavy chain polypeptide comprising a heavy chain variable region comprising CDRs having the amino acid sequences shown in residues 31–35, 50–66 and 99–107 of SEQ ID NO: 2 forms an antigen-combining region that binds the $\alpha_v$ subunit of $\alpha_v\beta_3$ and $\alpha_v\beta_5$; and
   (b) a nucleic acid sequence that is fully complementary to the entirety of said nucleic acid sequence encoding an immunoglobulin light chain polypeptide.

9. The isolated nucleic acid molecule of claim 8, wherein said immunoglobulin light chain polypeptide comprises the amino acid sequence shown in SEQ ID NO: 7.

10. The isolated nucleic acid molecule of claim 9 having the sequence shown in SEQ ID NO: 6.

11. The isolated nucleic acid molecule of claim 8, wherein said immunoglobulin light chain polypeptide comprises the amino acid sequence shown in SEQ ID NO: 10.

12. The isolated nucleic acid molecule of claim 11 having the sequence shown in SEQ ID NO: 9.

13. The isolated nucleic acid molecule of claim 8, wherein said immunoglobulin light chain polypeptide comprises the amino acid sequence shown in SEQ ID NO: 29.

14. The isolated nucleic acid molecule of claim 13 having the sequence shown in SEQ ID NO:28.

15. The isolated nucleic acid molecule of claim 8, wherein said immunoglobulin light chain polypeptide comprises the amino acid sequence shown in SEQ ID NO: 31.

16. The isolated nucleic acid molecule of claim 15 having the sequence shown in SEQ ID NO: 30.

17. A recombinant plasmid comprising the nucleic acid of claim 8.

18. An isolated host cell comprising the plasmid of claim 17.

19. An isolated host cell comprising a nucleic acid sequence encoding an immunoglobulin heavy chain polypeptide comprising a heavy chain variable region comprising complementarity determining regions (CDRs) having the amino acid sequences shown in residues 31–35, 50–66 and 99–107 of SEQ ID NO: 2 and further comprising a nucleic acid sequence encoding an immunoglobulin light chain polypeptide comprising a light chain variable region comprising complementarity determining regions (CDRs) having the amino acid sequences shown in residues 24–34, 50–56 and 89–97 of SEQ ID NO: 7, wherein said immunoglobulin heavy chain polypeptide and immunoglobulin light chain polypeptide when operatively combined form an antigen-combining region that binds the $\alpha_v$ subunit of $\alpha_v\beta_3$ and $\alpha_v\beta_5$.

20. A process for the production of an antibody that binds the $\alpha_v$ subunit of $\alpha_v\beta_3$ and $\alpha_v\beta_5$ comprising culturing the host cell of claim 19 in a medium under suitable conditions of time and temperature and pH and recovering the antibody produced, wherein said antibody comprises said immunoglobulin heavy chain and immunoglobulin light chain polypeptides.

* * * * *